United States Patent
Lopez-Calle et al.

(10) Patent No.: US 7,425,425 B2
(45) Date of Patent: Sep. 16, 2008

(54) METHOD FOR THE DETECTION OF ENZYME-CATALYZED CLEAVAGE REACTIONS BY FLUORESCENCE SPECTROSCOPY

(75) Inventors: Eloisa Lopez-Calle, Hamburg (DE); Joachim Fries, Tornesch (DE); Joern Jungmann, Hamburg (DE)

(73) Assignee: Evotec Oai AG, Hamburg (DE)

( * ) Notice: Subject to any disclaimer, the term of this patent is extended or adjusted under 35 U.S.C. 154(b) by 0 days.

(21) Appl. No.: 11/432,768

(22) Filed: May 12, 2006

(65) Prior Publication Data

US 2007/0122863 A1 May 31, 2007

Related U.S. Application Data

(63) Continuation of application No. 10/466,552, filed as application No. PCT/EP02/00845 on Jan. 28, 2002, now abandoned.

(30) Foreign Application Priority Data

Jan. 26, 2001 (EP) .................... 01101869

(51) Int. Cl.
*C12Q 1/37* (2006.01)
(52) U.S. Cl. ................. 435/23; 435/24; 435/4
(58) Field of Classification Search ............. 435/23, 435/24, 4
See application file for complete search history.

(56) References Cited

U.S. PATENT DOCUMENTS 6,342,611 B1 * 1/2002 Weber et al. ............ 549/227
2001/0046668 A1 11/2001 Levine et al.

FOREIGN PATENT DOCUMENTS

| FR | 2 791 141 | 3/1999 |
| WO | WO 00/52199 | 9/2000 |
| WO | WO 00/72016 | 11/2000 |

OTHER PUBLICATIONS

Bergmann, F. and Bannwarth, W., "Solid Phase Synthesis of Directly Linked Peptide-Oligodeoxnucleotide Hybrids Using Standard Synthesis Protocols", Tetrahedron Letters, 36:11 (1995), 1839-42.
Levine et al., "Measurement of Specific Protease Activity Utilizing Fluorescence Polarization", Analytical Biochemistry, 247 (1997), 83-88.
Robles, J., "Synthesis and Enzymatic Stability of Phosphodiester-Linked Peptide-Oligonucleotide Hybrids", Bioconjugate Chem., 8 (1997), 785-88.
Robles, J. et al., "Towards Nucleopeptides Containing Any Trifunctional Amino Acid", Tetrahedron, 55 (1999), 13251-64.
Singh et al., "Fluorescence Polarization for Monitoring Ribozyme Reactions in Real Time", Biotechniques, 29 (2000), 344-51.

* cited by examiner

*Primary Examiner*—Ralph Gitomer
(74) *Attorney, Agent, or Firm*—Jacobson Holman PLLC

(57) ABSTRACT

A method involves the detection of enzyme-catalyzed cleavage reactions using modular chemical compounds as substrates for the enzymes involved, and detection is effected by use of molecular-weight-sensitive methods.

1 Claim, 20 Drawing Sheets

Process of search for active substances:
Screening for inhibitors for caspase-3

- Number of screened potential modulators: 193,146
- Modulator concentration: 17 μM
- Primary hit rate: 1.5%
- Number of identified active modulators: 229
- Average Z' value (data statistics): 0.8
- Dose-response analysis: 27 modulators with $IC_{50}$ values of below 50 μM identified

Fig.19

SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence

```
<220> FEATURE:
<223> OTHER INFORMATION: Synthesized

<400> SEQUENCE: 1

Gly Asp Glu Val Asp Gly Lys
 1               5

<210> SEQ ID NO 2
<211> LENGTH: 7
<212> TYPE: PRT
<213> ORGANISM: Artificial Sequence
<220> FEATURE:
<223> OTHER INFORMATION: Synthesized

<400> SEQUENCE: 2

Gly Ile Glu Thr Asp Gly Lys
 1               5

<210> SEQ ID NO 3
<211> LENGTH: 15
<212> TYPE: DNA
<213> ORGANISM: Artificial Sequence
<220> FEATURE:
<223> OTHER INFORMATION: Synthesized

<400> SEQUENCE: 3
ccccaccacc acccc                                                        15
```

METHOD FOR THE DETECTION OF ENZYME-CATALYZED CLEAVAGE REACTIONS BY FLUORESCENCE SPECTROSCOPY

This is a continuation of Ser. No. 10/466,552 filed Jan. 7, 2004 now abandoned, which is a 371 of PCT/EP2002/00845, filed Jan. 28, 2002, the disclosure of each of the foregoing being incorporated by reference herein.

The invention relates to methods for the detection of enzyme-catalyzed cleavage and linking reactions and to means, especially kits and substrates, for performing such methods.

Enzymatic cleavage reactions, such as, in particular, proteolytic reactions, are wide-spread in biochemistry and play a decisive role in the biological function of organisms. Therefore, it is an important task to monitor these reactions in suitable test methods, so-called assays. The functionality of an assay is critically dominated by its reliability and reproducibility. Especially to assay systems employed in the high-throughput screening for novel pharmacologically active substances, very high standards are to be applied in this respect, since the time which remains for performing the assay and, in particular, for detecting a measuring point is extremely short. The currently known assay systems and substrates for proteolytic reactions, in particular, do not meet these demands in many respects.

For example, known assays include assays for non-specific proteolytic enzymes on the basis of bacterial luciferase as a substrate (Njus et al., Analytical Biochemistry 61, 280-287, 1974); these assays naturally fail when enzymes having a precisely defined substrate specificity are to be examined.

In addition, the prior art describes assay systems with the related substrates which are based on fluorogenic or chromogenic principles using a dye for coupling to the substrate. The fluorogenic principle is based on the synthesis of an amide from a primary or secondary amine moiety of a dye with the carboxy group of an amino acid. The electron-withdrawing property of the carboxy group causes the electron density in the dye system to be reduced (incidentally, this also holds for the chromogenic principle) and thus the chromophorous system to be impaired, i.e., the dye loses its dye properties. A peptide having an arbitrary sequence can now be synthesized onto the coupled-on amino acid. At any rate, it is critical that the cleavage site for the proteolytic reaction is the amide bond between the dye and the first amino acid. The cleavage of this bond restores the electronic system of the dye and thus its dye properties (chromogenic system), and in the case of a fluorescent dye, it is again capable of emitting light quanta upon appropriate excitement (fluorogenic system). Such a system has been disclosed, for example, in U.S. Pat. Nos. 4,557,862 and 4,640,893, which describe a class of rhodamine derivatives which are not fluorescent in the form of bisamide substitution products while the monoamide substitution products exhibit a high degree of fluorescence. Thus, the cleavage of a single specific amide bond by specific proteases converts the non-fluorescent derivative into a fluorescent derivative, which serves as a read-out parameter for the proteolytic reaction. Applications of these techniques for serine proteases have been described, for example, by Leytus et al. (Biochem. J. 209, 299-307, 1983; Biochem. J. 215, 253-260, 1983). The techniques have also been employed for cysteine protease assays, for example, for the detection of the caspase enzyme class, which is relevant to the detection of apoptotic processes, see, for example, Hug et al. (Biochemistry 38, 13906-13911, 1999), Weber et al. (WO 99/18856), Xiang et al. (Proc. Natl. Acad. Sci. USA, 93, 14559-14563, 1996), and Talanian et al. (The Journal of Biological Chemistry, 272, 9677-9682, 1997).

The disadvantages of these techniques reside in the very limited selection of dyes which can be linked with amino acids in the way described and can thus reversibly lose their dye properties. The few known examples are rhodamine 110 and 7-aminomethylcoumarin. The synthesis of these molecules is very difficult in part. In addition, the amide bond between the dye and the amino acid is not a peptidic bond as in real biological substrates of a proteinase. This results in a dramatic deterioration of molecular recognition by the enzyme. Therefore, it is necessary here to work in a concentration range which is not tolerable for single-molecule techniques, for example, on confocal basis. The read-out parameter is fluorescence intensity, which is difficult to standardize, so that the parameters of the proteolytic reaction to be examined can be derived therefrom only with high difficulty. A high amount of background fluorescence as encountered with these substrates also leads to a reduction of the usefulness of such a system. Due to the impaired electronic system of the dye prior to the occurrence of an enzymatic reaction, there is no emission, and thus it cannot be checked how much substrate has been charged.

Further, the prior art describes assays using substrates which are labeled with two dye molecules. Proteolytic assays of this kind contain a peptide sequence which preferably bears a specific cleavage sequence and is labeled with two dye markers on both ends of the peptide chain. The proteolytic reaction decomposes the peptide chain into two (when there is one cleavage site) or more fragments and spatially separates the two dye markers. In the case of heterogenic labeling, this is a pair of dyes which is capable of performing fluorescence resonance energy transfer (FRET). The proteolytic reaction destroys this FRET effect, and the two spectrally separated dyes exhibit their respective characteristic fluorescence properties, which had previously been interacting in the uncleaved peptide chain. FRET measurements have been performed, for example, on fluorogenic substrates for interleukin-1β converting enzyme (ICE) (Pennington et al., Peptide Research, 7, 72-76, 1994). The FRET effect is based on the mutual spatial orientation of the two partners involved, so that fluctuations in their distance, as occur in a peptide chain which is not spatially fixed, also lead to fluctuations in the signal, which prevents an accurate detection. Another disadvantage is the fact that the cleavage site must be between the two dyes of the FRET pair. Due to this spatial proximity, interference with the enzymatic bond may occur. In homogeneous labeling, two identical dye molecules are employed, for example tetramethylrhodamine, as described by Packard et al. (J. Phys. Chem. B 102, 1820-1827, 1998; J. Phys. Chem. B 102, 752-758, 1998; Biophysical Chemistry, 67, 167-176, 1997). In an aqueous environment, tetramethylrhodamine tends to undergo hydrophobic interactions which lead to dimerization of the dye and to a loss of its fluorescence properties. This means that the two dye molecules dimerize intramolecularly in common on one peptide and that this intramolecular dimerization is reverted only after the cleavage of the peptide chain. Although intermolecular dimerization after the occurrence of the cleavage is still possible, it is little relevant due to the concentration conditions in which the assay is effected. However, the dimerization of the dyes in the uncleaved condition is not complete either, so that a detectable background signal remains. Further, naturally, only dyes having hydrophobic properties can be used, because only these exhibit a tendency to dimerize, which results in substantial problems in the design of an assay which has to be employed in a biologically compatible and thus aqueous environment.

The prior art further describes proteolytic assays on the basis of fluorescence anisotropy. These work according to the principle that small fragments labeled with fluorescent dyes have a higher mobility after the proteolytic reaction and thus exhibit a faster rotation than that of a whole molecule prior to the reaction. On the one hand, the whole molecule can be a large protein which is randomly labeled with a high degree of labeling and which does not have a specific cleavage sequence for a particular protease. The protein is cleaved into fragments of which some fraction bears fluorescence markers. Such an assay which is based on the determination of fluorescence polarization as the detection method of choice as well as suitable substrates have been described, for example, by Maeda (Analytical Chemistry 92, 222-227, 1979). On the other hand, it may be a peptide having a, preferably specific, cleavage sequence and bearing a dye on one side and a biotin molecule on the other side. Through a biotin/(strept)avidin interaction, a very large complex having a high anisotropy is formed. The specific cleavage sequence which has been incorporated into the peptide is cleaved by the proteolytic reaction to form a small dye-bearing peptide fragment (see, for example, Bolger et al., BioTechniques 17, 586-589, 1994; Levine et al., Analytical Biochemistry 247, 83-88, 1997). However, depending on the protease employed, the (strept) avidin protein may also be attacked, so that there is no specificity since a proteolytic reaction which is not specific for the incorporated cleavage sequence may also mimic a corresponding reaction by the cleavage of the (strept)avidin. Even by the later addition of (strept)avidin, this disadvantage cannot be removed, so that this system may be useless, depending on circumstances. Anyway, when (strept)avidin is added later, only an end-point determination can be performed, and it is not possible to monitor the course of the reaction. Such a biotinylated substrate which is treated with (strept)avidin only after the enzymatic reaction has occurred in order to enable detection is not suitable for kinetic experiments because the reaction also tends to be stopped upon the addition of (strept)avidin. Thus, different reaction times could be realized only by a corresponding number of reactions. But even the mentioned stopping effect cannot be calculated, as shown in our own experiments with caspase-3 in which an enzymatic conversion of the caspase-3 substrate to which (strept)avidin had been added took place against expectations. Thus, to conclude, such assay systems do not meet the demands with respect to reliability of the results obtained and robustness in performance.

Therefore, it is the object of the present invention to provide universally useful methods for the detection of enzymatic cleavage and linking reactions as well as corresponding means which do not have the above mentioned drawbacks and are suitable, in particular, for use in high-throughput methods for the screening of pharmacologically active modulators of enzymatic reaction(s).

These objects are achieved by substrates, kits and assay methods according to the independent claims.

Thus, in a first aspect, the invention relates to a method for the detection of enzyme-catalyzed cleavage reactions, comprising the following steps:

a) providing a modular chemical compound containing the following sequence motif:

Z-X-Y or Y-X-Z wherein Z comprises a module with a selectable molecular weight which is inert with respect to said enzymatic cleavage reaction;

X comprises a module with n cleavage sites $S_1$ to $S_n$ which can be cleaved by said enzyme-catalyzed cleavage reaction into at least two cleavage products containing $X_1$ and $X_{n+1}$, respectively, and having defined molecular weights, n being an integer of $\geq 1$; and Y comprises a reporter module;

as a substrate for said enzyme(s) catalyzing said cleavage reaction(s);

b) incubating the compound with said enzyme(s) catalyzing said cleavage reaction(s) to form at least two cleavage products which contain $Z-X_1$ and $X_{n+1}-Y$ or $Y-X_1$ and $X_{n+1}-Z$ wherein the molecular weight of the cleavage product containing $Z-X_1$ or $X_{n+1}-Z$ is at least fifty percent of the total molecular weight of the substrate;

c) detecting the enzymatic activity or activities by determining the cleavage product containing the reporter module Y by means of a molecular-weight-sensitive method.

Further, according to the invention, a generic modular substrate is provided which contains the following sequence motif:

Z-X-Y or Y-X-Z wherein X comprises a module with n cleavage sites $S_1$ to $S_n$ which can be cleaved by at least one enzyme-catalyzed cleavage reaction into at least two cleavage products containing $X_1$ and $X_{n+1}$, respectively, and having defined molecular weights;

Y comprises a reporter module; and

Z comprises a module with a selectable molecular weight which is inert with respect to said enzymatic cleavage reaction(s) and whose molecular weight has been selected such that the molecular weight of the cleavage product containing $Z-X_1$ or $X_{n+1}-Z$ after the enzymatic reaction has occurred is at least fifty percent of the total molecular weight of the generic substrate.

For example, the substrate can be provided in the form of a kit. In addition to a substrate or several different substrates according to the invention, such a kit may optionally also comprise at least one enzyme for catalyzing said cleavage reaction(s) at the cleavage sites $S_1$ to $S_n$ as well as cosubstrates, cofactors, modulators, buffers and/or reagents for stopping said enzymatic reaction.

Of particular importance to the method according to the invention and for the substrate is, on the one hand, the use of a module Z which is inert with respect to the enzymatic cleavage reaction. Thus, when a non-inert module Z were used, cases could occur, for example, in which reaction products are formed which are but slightly distinct with respect to their molecular weights and could not be read out by molecular-weight-sensitive methods, or only so with a high inaccuracy. If the module Z were cleaved at several sites by the enzymatic activity, a large number of reaction products with different molecular weights would be produced, resulting in a "smeared" detection signal. On the other hand, it is further of particular importance to ensure a sufficiently high difference between the molecular weight of the substrate and that of the cleavage product containing the reporter module Y in order to enable a high detection accuracy. Especially in High-throughput screening (HTS) methods for pharmacologically effective modulators of the enzymatic reaction, the detection time is often limited to only a few seconds per modulator, so that a more than average detection accuracy is indispensable.

According to the invention, these requirements are ensured by the fact that the molecular weight of the module Z is to be selected such that the molecular weight of the cleavage product containing Z-$X_1$ or $X_{n+1}$-Z after the enzymatic reaction has occurred is at least fifty percent of the total molecular weight of the generic substrate.

Due to the modular composition of the substrate according to the invention, it is possible to adapt it in a simple and inexpensive way to the enzyme(s) to be tested and to the detection method employed. The identities of Z and Y are subject to some flexibility, in principle, which can be utilized for designing an optimum assay. Due to the modular concept, substrates can be assembled for any desired cleavage reactions having a defined cleavage sequence/cleavage region. The assay designer can have different modules Z and Y on stock, so to speak, in order to be able to quickly incorporate any desired cleavage regions which can then be tested in enzymatic reactions.

In a particularly advantageous way, the components of the substrate are covalently linked to each other. The particular importance of the covalent linkage between the substrate components is impressively seen in a comparison with the (strept)avidin/biotin system of the prior art. For example, in a substance library which is to be tested in high-throughput screening, substances could exist which affect the binding of (strept)avidin to biotin. In a screening for enzyme inhibitors or enzyme activators, such substances would appear as false negative or false positive hits. However, in view of the immense costs of the further optimization of hits, an elimination of false-positive hits is of utmost commercial importance to the pharmaceutical industry.

In a preferred embodiment, X comprises a module with one cleavage site $S_1$ which can be cleaved by the enzyme-catalyzed cleavage reaction into two cleavage products containing $X_1$ and $X_2$, respectively, and having defined molecular weights. However, in a further embodiment, there are also provided a substrate and a corresponding detection method in which X is a module having several cleavage sites $S_1$ to $S_n$, wherein n>1. Thus, n+1 cleavage products having defined molecular weights are produced by the enzymatic cleavage reactions. Thus, the substrate may contain, for example, two cleavage sequences $S_1$ and $S_2$ which can be cleaved by the enzymes $E_1$ and $E_2$. The same substrate can be used for respective incubations with either of the enzymes $E_1$ or $E_2$. The formation of the respective products, Z-$X_1$ and $X_2X_3$-Y or Z-$X_1X_2$ and $X_3$-Y, can be detected by a molecular-weight-sensitive method. This embodiment of the substrate with several, especially two, cleavage sites enables, firstly, to perform several drug discovery programs (search for modulators of enzyme $E_1$ or enzyme $E_2$) with only one substrate and, secondly, to determine the selectivity of modulators. In this latter case, it is examined whether a modulator of enzyme $E_1$ is also a modulator of enzyme $E_2$, or whether a modulator of enzyme $E_2$ is also a modulator of enzyme $E_1$. This is an important issue in the development of pharmaceutical products, since any undesirable side-effects of a modulator of $E_1$ on further enzymes, such as $E_2$, can be detected.

In a preferred embodiment, the substrate has such a design that the molecular weight of Z is selected such that the molecular weight of Z-$X_1$ and that of $X_{n+1}$-Z are at least about 60% of the total molecular weight of the substrate Z-X-Y or Y-X-Z. However, it is often preferred that the molecular weight of Z-$X_1$ and that of $X_{n+1}$-Z are at least about 70%, especially at least about 80%, more preferably at least about 90%, of the total molecular weight of the substrate. Thus, depending on the detection efficiency of the molecular-weight-sensitive detection method employed, the optimum molecular weight difference or molecular volume difference between the educt and products formed after the enzymatic cleavage reaction can be adjusted. Thus, for example, particularly suitable detection methods are those which are based on fluorescence polarization or fluorescence anisotropy determinations, or fluorescence correlation spectroscopy. The detection can preferably by performed by using a confocal optical design, by which any background signals can be clearly reduced due to the very small measuring volumes (down to the femtoliter range). With the substrate according to the invention, which thus preferably comprises a fluorescence marker as the reporter module Y, a number of molecular parameters can be read out directly or indirectly. The correlation time, i.e., the characteristic time required for a molecule to perform some defined movement, is directly related to the volume of the molecule. The rotational correlation time φ is given according to the following relationship:

$$\phi = \eta V/RT$$

where η: viscosity
V: volume of the molecule
R: general gas constant
T: temperature in K This shows that the following holds under typical assay conditions at a fixed temperature in a solvent having a fixed viscosity: φ=η times constant.

The parameter r, the anisotropy of the fluorescence light, which is readily available experimentally, is related to the rotational correlation time φ according to the Perrin equation:

$$r = r_0/[1+(\tau/\phi)]$$

where: $r_0$: anisotropy at the time t=0
τ: fluorescence lifetime of the dye.

In the method according to the invention, a change of the volume or molecular weight of the chemical compound comprising the dye-bearing reporter module Y is caused by the cleavage reaction (e.g., proteolytic reaction). It is to be noted, in particular, that the anisotropy can not only be read out as a sum signal, but can also be analyzed on the level of individual molecules. This means that the absolute concentration of the substrate cleaved, for example, by proteolysis, and having a high rotational correlation time (fast rotation) and the absolute concentration of (as yet) unreacted substrate having a low correlation time (slow rotation) can be determined directly from the sample. External calibration can be omitted, since the ratio of the two species can be determined directly and thus the conversion can be calculated in a simple way. An analogous consideration applies to the behavior of the substrate according to the invention when detection systems are used which establish a translational diffusion correlation time. Thus, fluorescence correlation spectroscopy (FCS) can be used to establish the diffusion constant of the fluorescent molecule, which directly depends on the mass of the molecule and by means of which an absolute concentration of the two species can also be detected.

In order to achieve the inert character of the preferably polymeric fraction Z in the total substrate, it is suggested according to the invention to select Z and X from different classes of substances. Thus, for example, a proteolytic enzyme reaction could be examined by means of molecular-weight-sensitive optical methods in which X is an amino acid sequence with suitable cleavage sites for the enzyme employed, and Z belongs to a different class of substances, i.e., is not a peptide or protein. In this case, it is particularly advantageous to construct Z from nucleotides, a double-stranded nucleic acid being particularly preferred. Such a substrate is shown illustratively in FIG. 1. However, any other, preferably hydrophilic, polymer is also suitable as the Z module. Hydrophilic Z modules are particularly preferred if the assay is to be performed in aqueous solution in order to take biological conditions into account.

In contrast to previously known systems, the substrate according to the invention and its application in the cleavage assay according to the invention exhibits the following advantages:

1. Clearly defined cleavage products after the cleavage reaction, such as a proteolytic reaction: Only those cleavage products which are clearly defined by the structure of the substrate and which have unambiguous molecular weights are formed.
2. Homogeneous signal distribution due to a defined molecular structure: Since clearly defined fragments are present after the cleavage reaction, such as a proteolytic reaction, one unambiguous rotational or diffusion correlation time is to be expected for the fragment bearing the dye. A polydispersity of the products with an associated "smearing" of the detected signal as often observed in the prior art is avoided.
3. Modular structure: The substrate according to the invention has a modular structure and can be adapted in many ways to the problem to be examined:
   Reporter module: When optical detection is used, the dye which is suitable in terms of the detection technology and in chemical and photophysical terms can be selected from a wide variety of dyes capable of coupling (amine-reactive, thio-reactive, carboxylic-acid-reactive etc.). Thus, there may be used, for example, coumarins, fluoresceins, rhodamines, xanthenes, oxazines, cyanines and the like as well as their derivatives.
   Module X with cleavage site: Any cleavage site, which preferably can be synthetically produced, can be incorporated, i.e., any enzyme, such as a protease with a known recognition or cleavage sequence, can be specifically and selectively examined. Thus, it is possible to specifically offer a substrate for a selected protease in a mixture of different proteases and to specifically study the reaction of this protease.
   The module Z (for example, a polymer, especially an oligonucleotide) can be freely selected, and its length/mass can be adjusted according to requirements in terms of detection technology. Also, hybridizations to DNA sequences in the assay can be used, if desired. Each and every module can contain different classes of substances, for example, the module Z can comprise a nucleic acid and a cyclohexanoic acid derivative (see Examples).
4. Linear or rigid structure of the substrate: Due to the stretched structure of a substrate as described, for example, in FIG. 1, especially when a DNA double strand is used, it is ensured that no influencing of the enzymatic, especially proteolytic, reaction occurs from a molecular interaction in the form of spatial contacts between the Z and X modules (e.g., the oligonucleotide and peptide portions in FIG. 1).
5. The water-solubility can be selectively adjusted. Thus, a high water-solubility can be achieved, in particular, by using a polyanionic oligomer moiety as the Z module. For biological assay systems in an aqueous environment, a high water-solubility of the substrate is naturally necessary and advantageous.
6. Direct monitoring of the reaction course: The substrate offers the possibility of observing the enzymatic cleavage reaction during the course of the reaction and thus to perform kinetics studies.
7. The substrate can be detected per se (cf. prior art with fluorogenic/chromogenic principles).
8. The module Z can be designed in such a way that it may also serve as (i) a recognition site for enzyme binding (e.g., binding of particular restriction endonucleases) or (ii) a binding site for factors influencing the enzyme binding or activity.
9. The reporter module Y can be spatially separated from the cleavage region (cf. prior art with fluorogenic/chromogenic principle; FRET).

Further, in another aspect, the invention relates to a method for the detection of enzyme-catalyzed linking reactions, comprising the following steps:

a) providing the following chemical compounds:

$Z-X_1$ and $X_{n+1}-Y$ and optionally $X_2$ to $X_n$;

or $Y-X_1$ and $X_{n+1}-Z$ and optionally $X_2$ to $X_n$;

wherein Z comprises a module with a selectable molecular weight which is inert with respect to said enzymatic linking reaction;

$X_1$ comprises a modular building block which can be linked by said enzyme-catalyzed linking reaction(s) directly with $X_{n+1}$ in the case where n=1, or optionally indirectly through at least one modular building block selected from $X_2$ to $X_n$ in the case where n>1;

$X_{n+1}$ comprises a modular building block which can be linked by said enzyme-catalyzed linking reaction(s) directly with $X_1$ in the case where n=1, or optionally indirectly through at least one modular building block selected from $X_2$ to $X_n$ in the case where n>1;

Y comprises a reporter module;

n is an integer of $\geq 1$; and the molecular weight of $X_{n+1}-Y$ or $Y-X_1$ is at most fifty percent of the total molecular weight of the linked product formed;

as a substrate for said enzyme(s) catalyzing said cleavage reaction;

b) incubating the compound with said enzyme(s) catalyzing said linking reaction(s) to form linked products

Z-X-Y or

Y-X-Z wherein X comprises the modular building blocks $X_1$ and $X_{n+1}$ and optionally at least one modular building block selected from $X_2$ to $X_n$;

c) detecting the enzymatic activity or activities by determining the linked product containing the reporter module Y by means of a molecular-weight-sensitive method.

In a preferred embodiment of this method, two modular building blocks $X_1$ and $X_2$ are directly linked with each other by said enzyme-catalyzed reaction. However, it is also possible to indirectly link $X_1$ and $X_{n+1}$ with each other through a modular building block $X_2$. A further embodiment of the method according to the invention consists in the indirect linking of $X_1$ and $X_{n+1}$ with each other through a plurality of modular building blocks. These building blocks are selected from the building blocks $X_2$ to $X_n$.

According to the invention, a kit of the following chemical compounds for the enzyme(s) catalyzing the linking reaction(s) is also provided for performing enzyme-catalyzed linking reactions:

$Z\text{-}X_1$ and $X_{n+1}\text{-}Y$ and optionally $X_2$ to $X_n$;

or $Y\text{-}X_1$ and $X_{n+1}\text{-}Z$ and optionally $X_2$ to $X_n$;

wherein
- $X_1$ comprises a modular building block which can be linked by said enzyme-catalyzed linking reaction(s) directly with $X_{n+1}$ in the case where n=1, or optionally indirectly through at least one modular building block selected from $X_2$ to $X_n$ in the case where n>1;
- $X_{n+1}$ comprises a modular building block which can be linked by said enzyme-catalyzed linking reaction(s) directly with $X_1$ in the case where n=1, or optionally indirectly through at least one modular building block selected from $X_2$ to $X_n$ in the case where n>1;
- Y comprises a reporter module;
- n is an integer of $\geq 1$; and
- Z comprises a module with a selectable molecular weight which is inert with respect to said enzymatic linking reaction and whose molecular weight has been selected such that the molecular weight of $X_{n+1}\text{—}Y$ or $Y\text{—}X_1$ is at most fifty percent of the total molecular weight of the linked product formed;

and optionally at least one enzyme catalyzing said linking reaction, cosubstrates, cofactors, modulators, buffers and/or reagents for stopping said enzymatic reaction.

Preferably, both with respect to the above mentioned method for the detection of linking reactions and to the description of the kit, the molecular weight of Z is selected such that the molecular weight of $Y\text{-}X_1$ or $X_{n+1}\text{-}Y$ is at most about forty percent, especially at most about thirty percent, preferably at most about twenty percent, more preferably about ten percent, of the molecular weight of the compound Z-X-Y or Y-X-Z. Thus, by analogy with the description of the method according to the invention for the detection of cleavage reactions, a substrate choice which is optimally adapted to the detection method can also be enabled in linking reactions.

As already discussed in the description of the substrate according to the invention for cleaving reactions, it is also preferred for these substrates for linking reactions that X and Z belong to different classes of substances. Thus, for example, they may respectively belong to the following classes of substances: nucleic acids, peptide nucleic acids (PNA), peptides, proteins, lipids, carbohydrates or derivatives of the above mentioned substances. In particular, these may be synthetic polymers.

It may be noted generally that all the stated substrates, kits and assays are particularly suitable for testing enzyme and/or modulator specificities, for testing enzyme and/or modulator activities, for the identification of modulators and/or substrates, for the detection of contaminations in chemical or biological samples, for the screening for pharmacologically active substances, or for diagnostic purposes. These applications can also be seen, in particular, from the Figures shown below and the related Figure descriptions.

Further, it is also generally desirable to select the module Z to have such a chemical structure as does not sterically interact with the cleavage or linking site. This can be enabled, in particular, by a rigid structure of Z, e.g., a linear structure, such as that of a polyanion. As already mentioned somewhere, it is particularly preferred to use a double-stranded nucleic acid or a derivative thereof.

In one embodiment, the enzyme catalyzing the reaction may be a hydrolase, especially a lipase, phosphatase, amylase, glycosidase, nucleosidase, peptidase, protease, amidase, pyrophosphatase, ATPase or phosphoamidase. The enzyme catalyzing the reaction may also be a lyase, especially a C—C, C—O, C—N or C—S lyase. In particular, it may be a (de)carboxylase, aldolase, dehydratase, ammonia-lyase, arginosuccinase or cysteine desulfhydrase. Further, the enzyme catalyzing the reaction may be, for example, a ligase, especially a C—O, C—S, C—N or C—C ligase. Illustratively, there may be mentioned an amino-acid activating ligase, acyl-CoA synthetase, glutamine synthetase or pyruvate carboxylase. In addition, transferases such as DNA or RNA polymerases may also be employed. Generally, it may be preferred to employ enzymes having substrate, group or steric specificity. As set forth in the Examples, the enzyme may also be, in particular, a caspase, such as caspase 3 or caspase 8. The substrate according to the invention then comprises a cleaving sequence specific for the respective caspase in its module designated with X, while the module designated with Z preferably belongs to a different class of substances, such as oligonucleotides.

In particular, the enzyme-catalyzed cleaving or linking reaction may be performed in the presence of one or more cosubstrates or cofactors. Also, one or more enzymes and/or substrates may be employed simultaneously or sequentially. In particular, the linking or cleaving reactions may be performed in the presence of modulators or potential modulators of enzymatic activity.

In particular, it is preferred to perform the methods according to the invention as homogeneous assays, i.e., without washing steps. Especially the fluorescence-spectroscopic detection methods described in more detail above allow such an approach in combination with the substrates according to the invention for cleaving or linking reactions. In order not to falsify the results, it may be desirable in special cases to detach the enzyme catalyzing the cleaving or linking reaction from the reaction product containing the reporter module Y, preferably (bio)chemically. Further, it is generally often advantageous to use a reporter module Y with a fluorescent dye.

BRIEF DESCRIPTION OF THE DRAWINGS

In the following, the invention is illustrated in an exemplary way by the Figures. Further, Examples are presented, especially of the synthesis of the substrates according to the invention.

Figure 1:
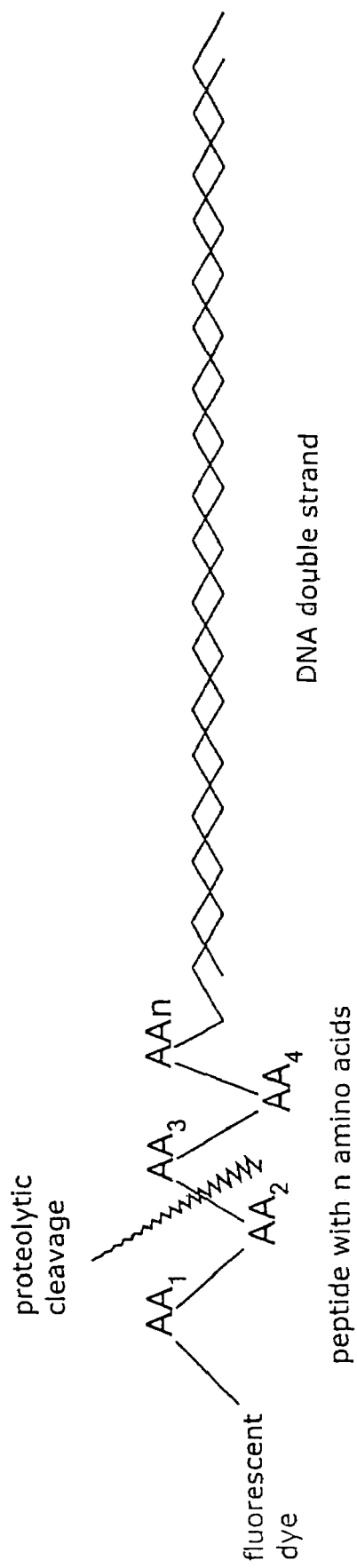
FIG. 1 shows the structure of an embodiment of the substrate according to the invention, wherein the fluorescent dye may be any dye that can be covalently coupled with an amino acid, especially coumarins, fluoresceins, rhodamines, xanthenes, oxazines, cyanines and the like, or derivatives thereof. The length of the peptide module is preferably from n=1 to n=100, more preferably to n=10. Within the peptide sequence, at least one combination of successive amino acids which is specific for a particular proteolytic reaction is preferably present. The recognition sequence of the respective protease can also be incorporated selectively and specifically here. The fragment formed upon the proteolytic cleavage which bears the DNA double strand is preferably such that its proportion in the total molecular weight of the molecule is at least 80%.
Figure 2:
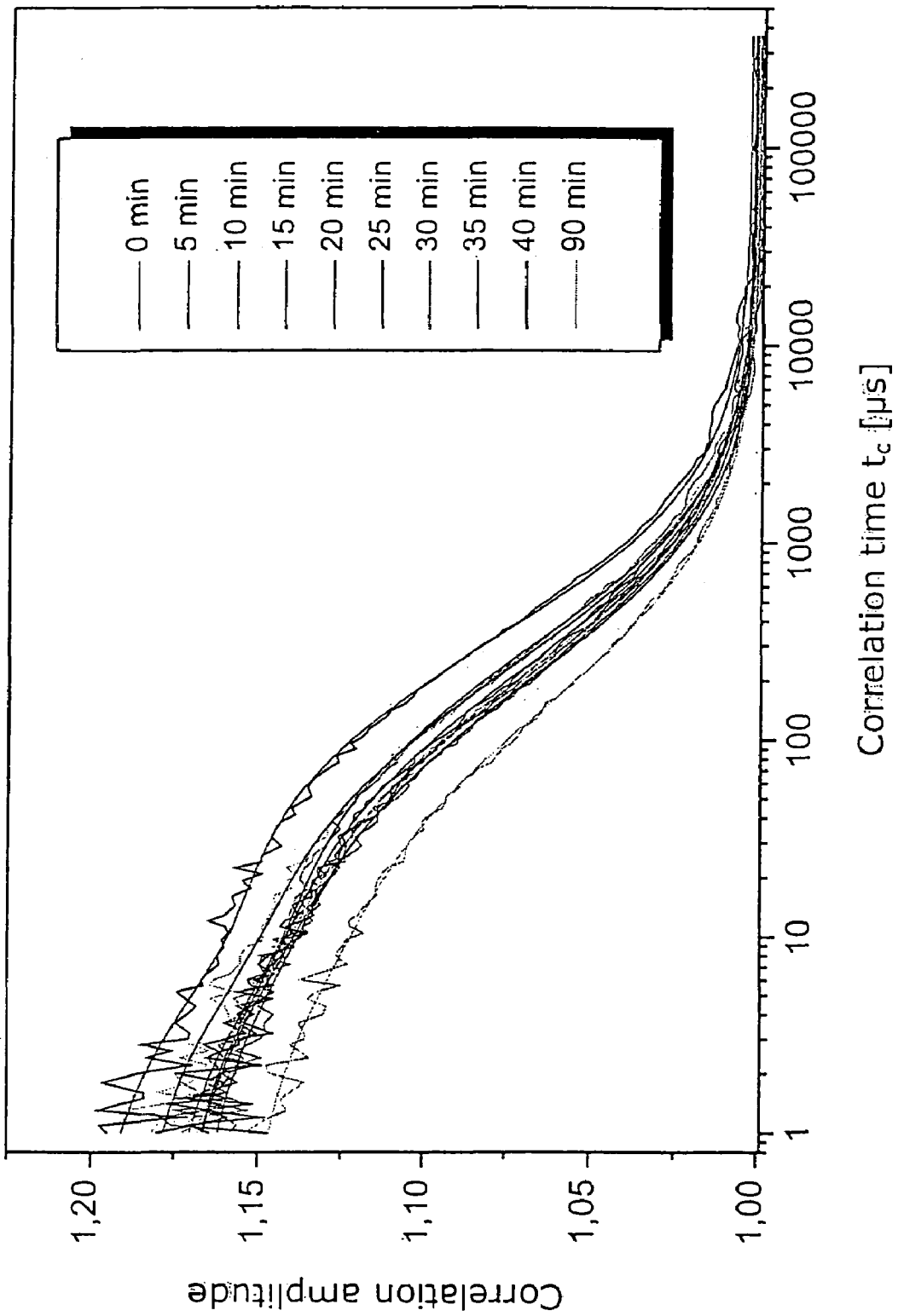

By means of the Example underlying FIG. 2, it shall be demonstrated how an embodiment of the substrate according to the invention which bears the specific recognition sequence of the caspase 3 protease is cleaved proteolytically. The proteolytic cleavage is monitored by measuring the diffusion time $\tau_D$ by means of fluorescence correlation spectroscopy (FCS). Thus, a 5 nM solution of the substrate described in Example 1 in a buffer (50 mM HEPES, pH 7.5, 100 mM NaCl, 10% saccharose, 0.1% CHAPS, 10 mM DTT) is incubated together with 1 nM caspase, and the course of the fluorescence correlation signal is observed as a function of time. The fitting of the measured curve to the correlation function (2 components) was effected with the values $\tau_{D1}$=313 ns (uncleaved substrate) and $\tau_{D2}$=70 μs (cleaved substrate). The reduction of the average diffusion time can already be seen from the change of the correlation curves in time.

Figure 3:
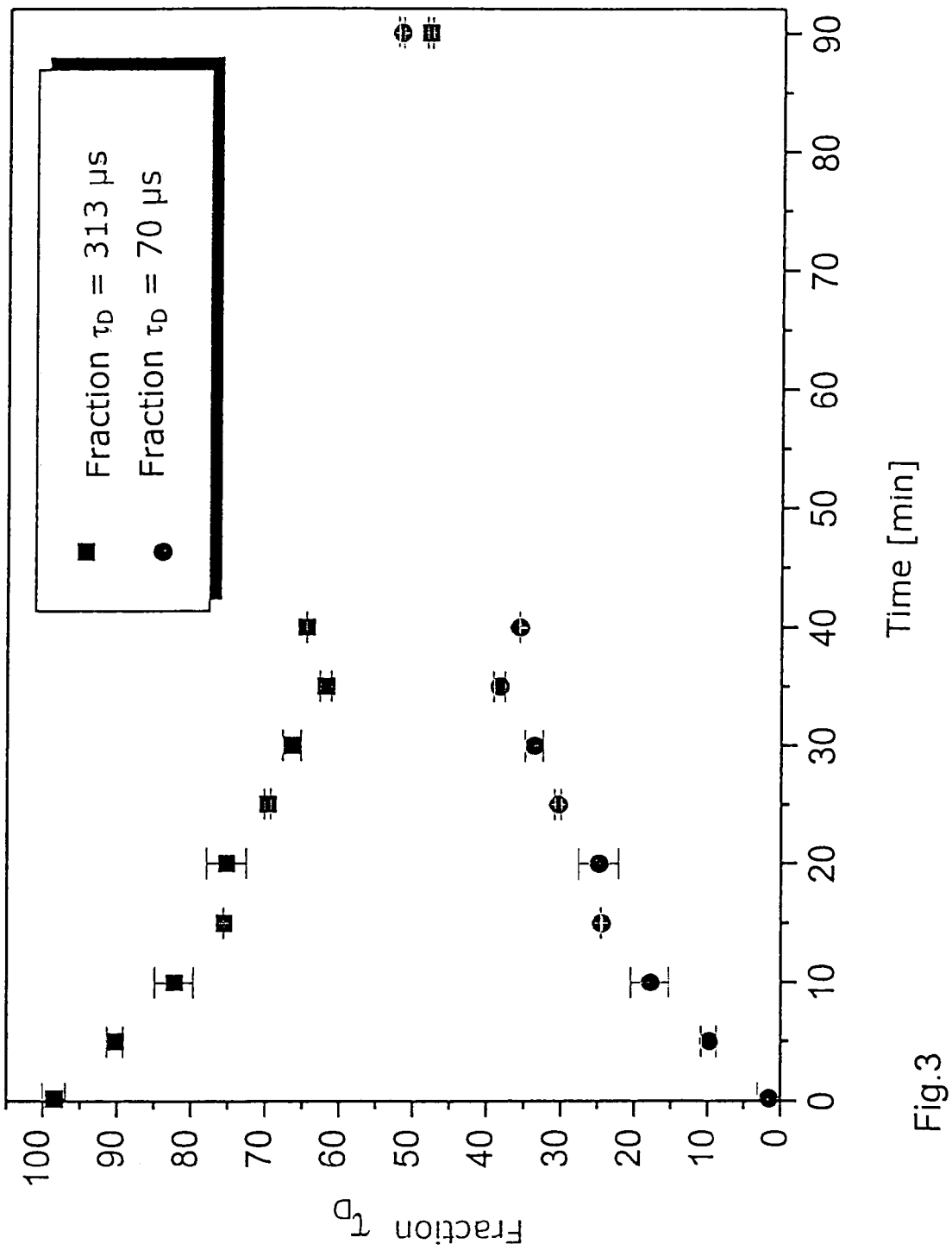

The exact analysis of the parameters mentioned under FIG. 2 result in the proportions of the individual diffusion times as plotted in FIG. 3 and thus in the proportions of the individual species of dye-bearing particles.

Figure 4:
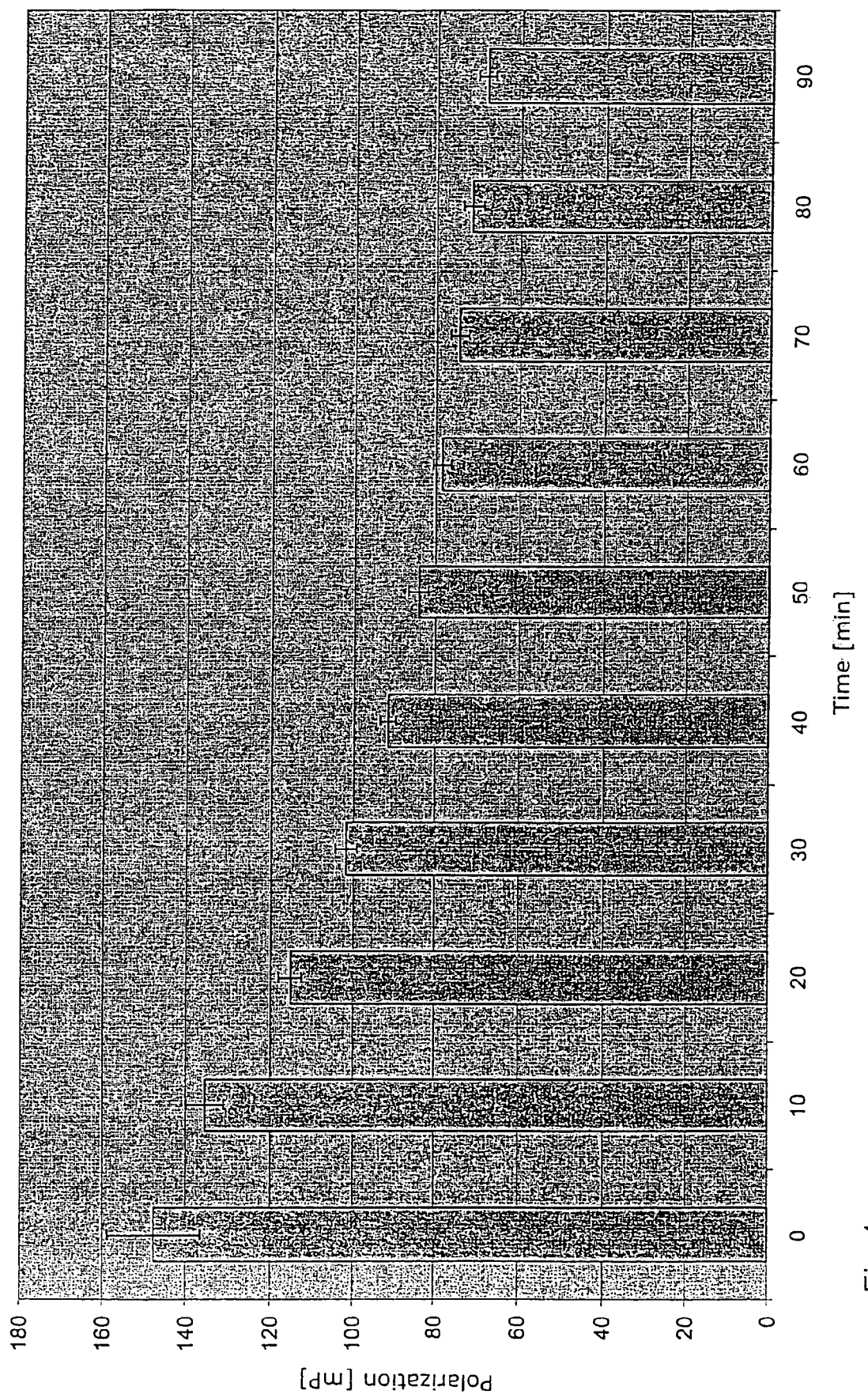

By means of the Example underlying FIG. 4, it shall be demonstrated how an embodiment of the substrate according to the invention which bears the specific recognition sequence of the caspase 3 protease is cleaved proteolytically. The proteolytic cleavage is monitored by measuring the fluorescence polarization. Thus, a 1 nM solution of the substrate described in Example 1 in a buffer (50 mM HEPES, pH 7.5, 100 mM NaCl, 10% saccharose, 0.1% CHAPS, 10 mM DTT) is incubated together with 1 nM caspase, and the course of the fluorescence polarization is observed as a function of time. The graph shows how the polarization of the sample decreases with time. The stated standard deviations respectively result from 25 measurements. The cause of this course resides in the cleavage of the substrate by the proteolytic activity of the caspase.

Figure 5:
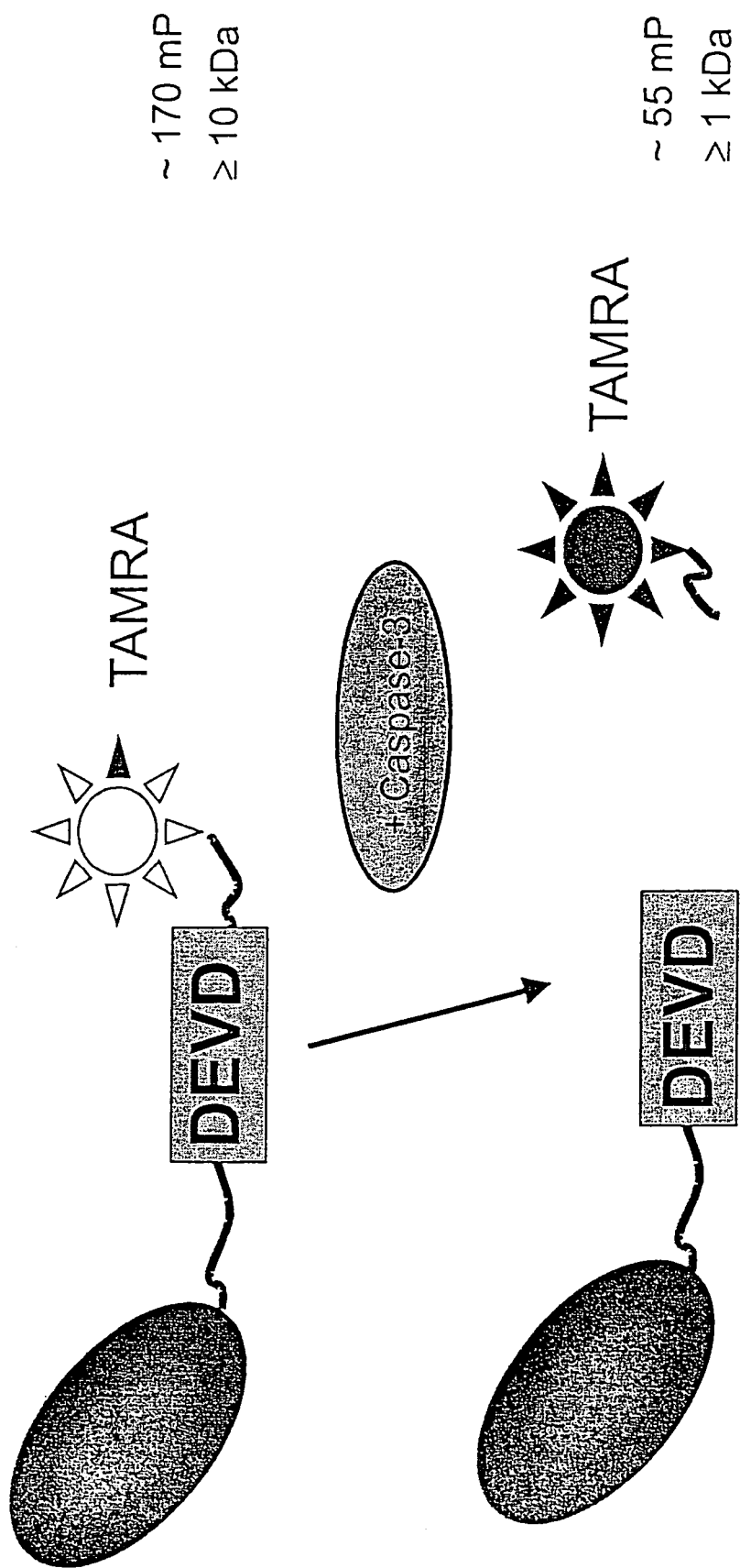

FIG. 5 shows an embodiment of the substrate according to the invention and its application in a caspase 3 assay. The tripartite substrate consists of a schematically represented polymer, a sequence to be cleaved containing the recognition sequence DEVD (in a one-letter code) which is typical of caspase 3, and the fluorescent dye TAMRA. A clear difference in the detected fluorescence polarization which is associated with the cleavage can be seen.

Figure 6:
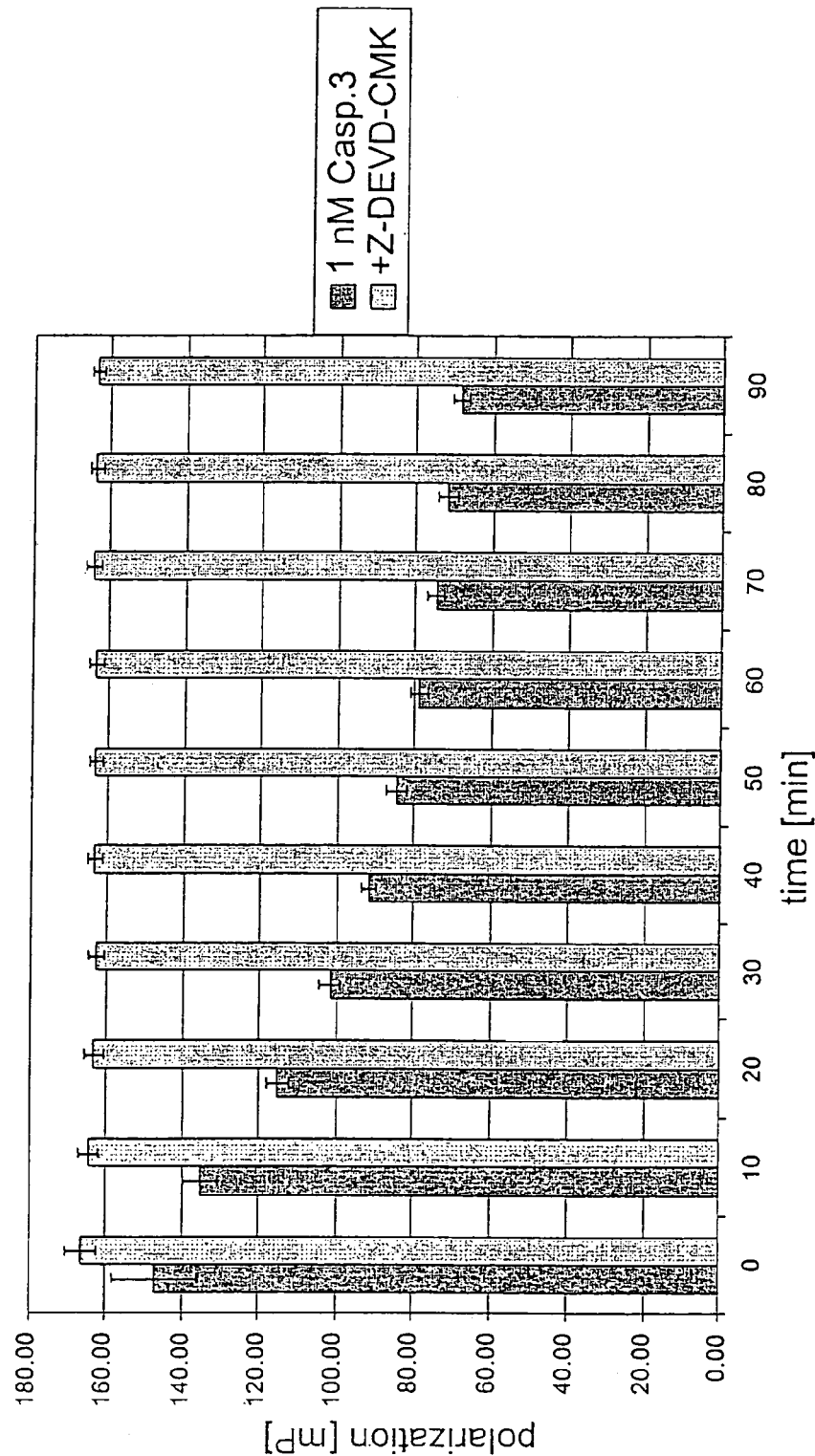

FIG. 6 shows the determination of the Z' factor, which is a measure of the signal-to-noise ratio of the assay using 10 nM substrate and applying a confocal detection set-up. The experiment provides the assay designer with information about (i) the dynamic region, (ii) the time window for a linear reaction, (iii) standard deviation, CV (data statistics) and (iv) Z' factor (comparison with inhibited reaction). These results permit the determination of the so-called "screening window" (could this assay be used for screening?). An excellent Z' factor of ≧0.83 is shown here already after 40 minutes.

Figure 7:
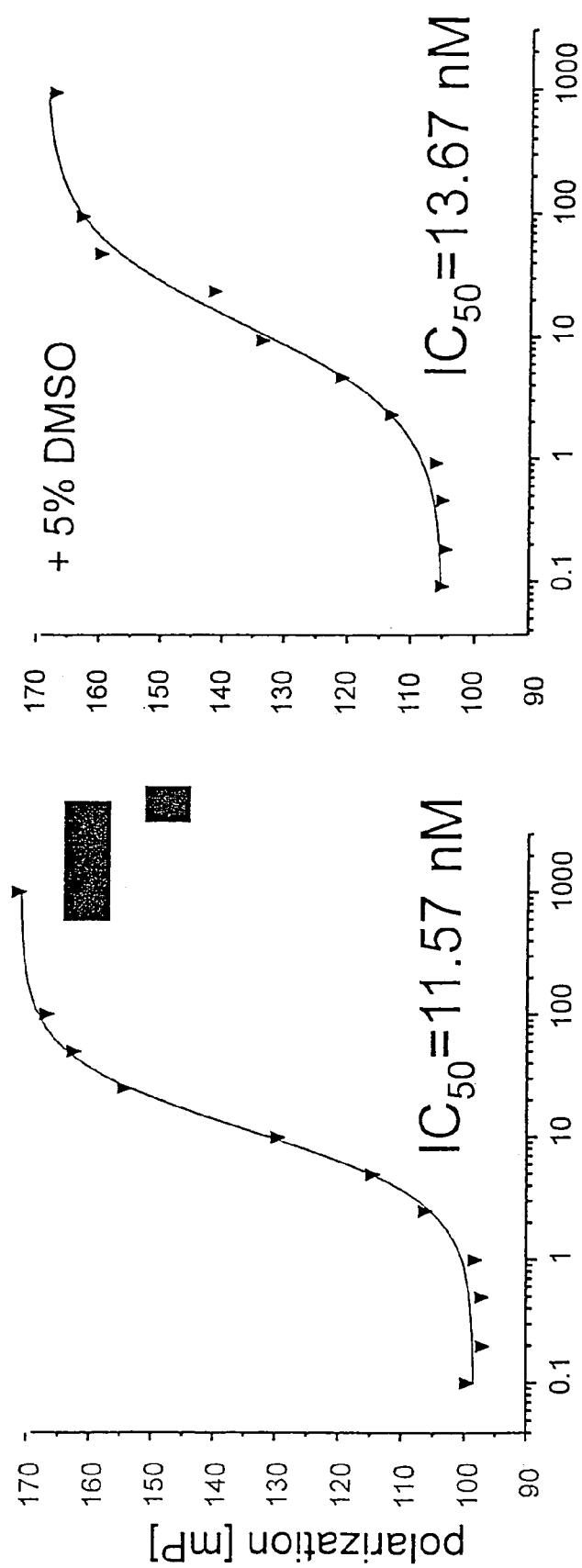

FIG. 7 shows the established $IC_{50}$ values. The Figure shows that an almost identical dose-response curve can be measured in the absence/presence of DMSO. Since compounds are usually dissolved in DMSO and a residual concentration is often unavoidable in HTS, such a test is important.

Figure 8:
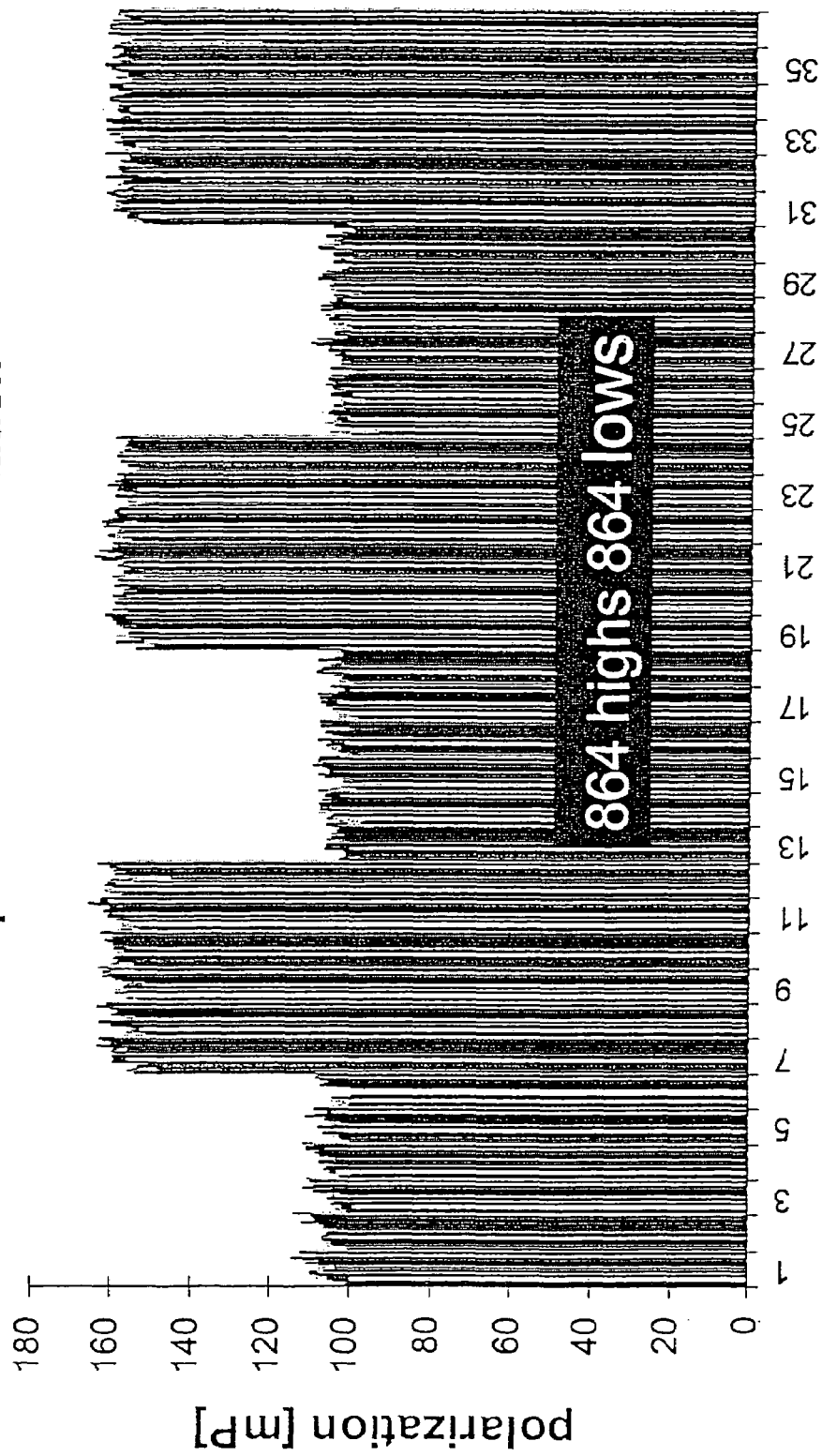

FIG. 8 illustrates the adaptation of the assay to a final volume of 1 μl in nanoti-tration plates. It is found that the so-called highs (in the presence of an inhibitor) and "lows" (in the absence of an inhibitor) are still readily distinguished, and the Z' factor is sufficient for employing the assay in a high-throughput screening for modulators of enzymatic activity which, if suitable, may be used later as pharmaceuticals.

Figure 9:
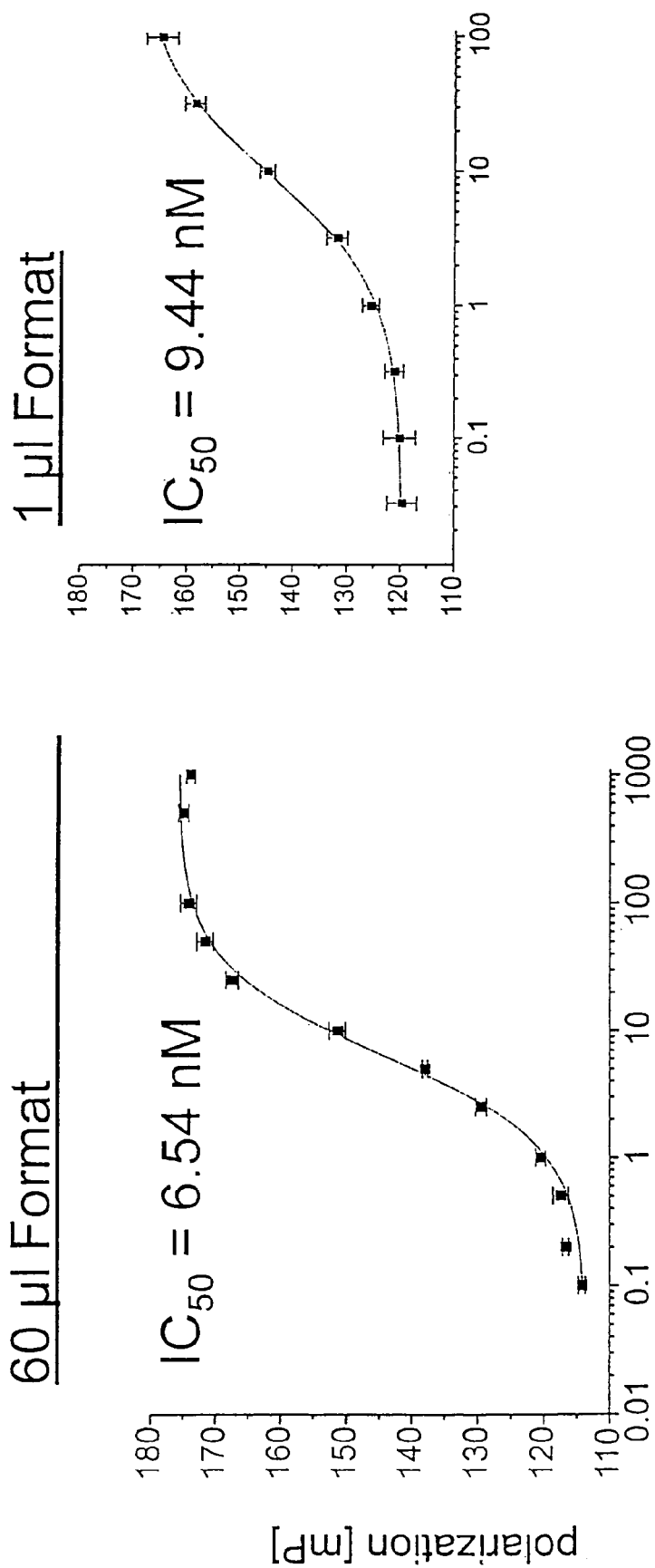

FIG. 9 shows a comparison between the $IC_{50}$ values in 60 μl and 1 μl assay formats with the addition of screening additives. The assay performance in the 1 μl format, which is advantageously employed in high-throughput screening due to the low consumption of substances, is comparable with the performance in assay development. Thus, the assay designer can release the assay for high-throughput screening for pharmacologically active substances.

Figure 10:
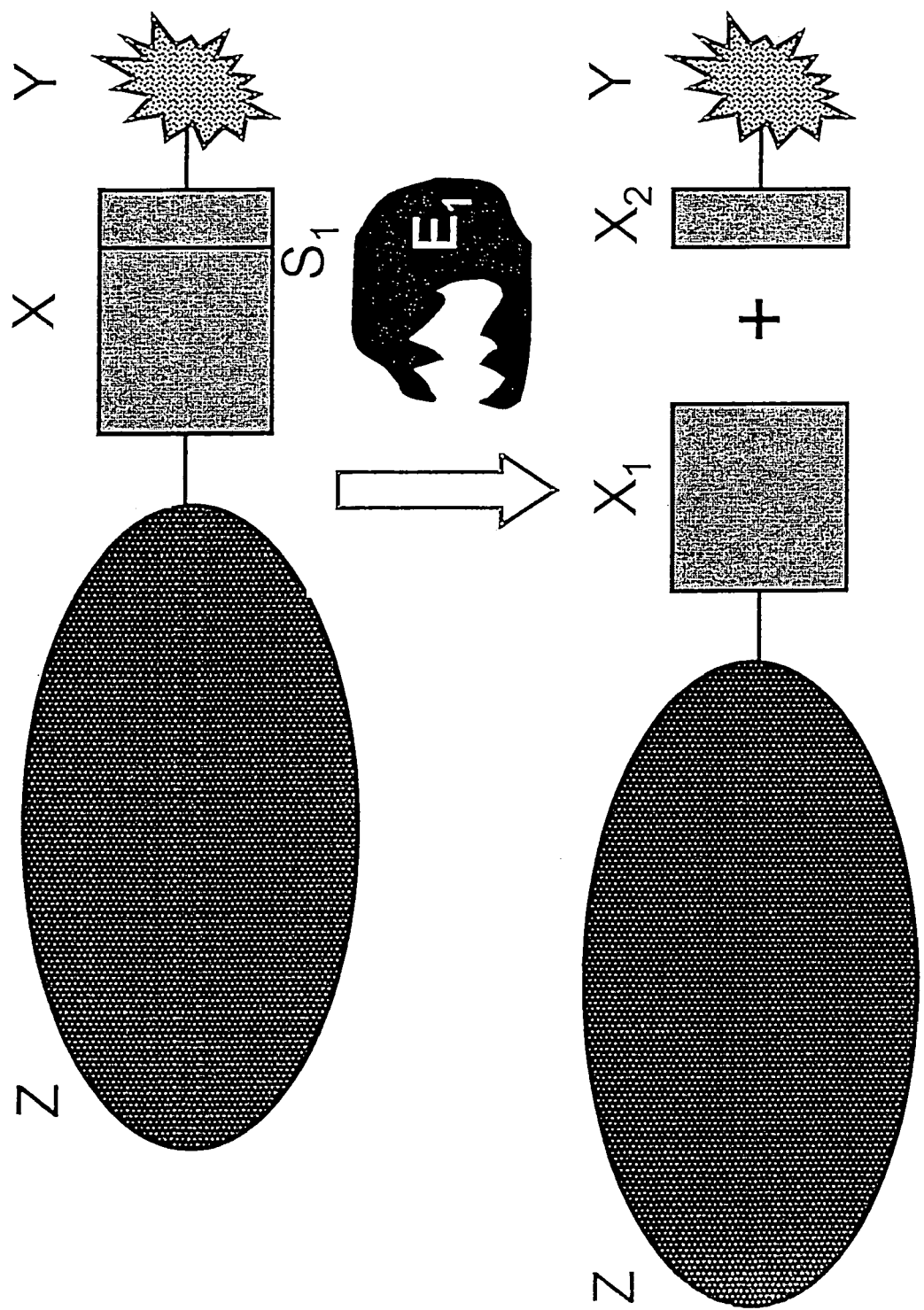

FIG. 10 schematically shows an embodiment of the substrate (Z-X—Y) according to the invention and its use in the detection of enzyme-catalyzed cleavage reactions. In this Figure, the substrate has a single cleavage site $S_1$. Upon cleavage by the enzyme $E_1$, the two cleavage products Z-$X_1$ and $X_2$—Y are formed. This reaction can be detected by a molecular-weight-sensitive method.

Figure 11:
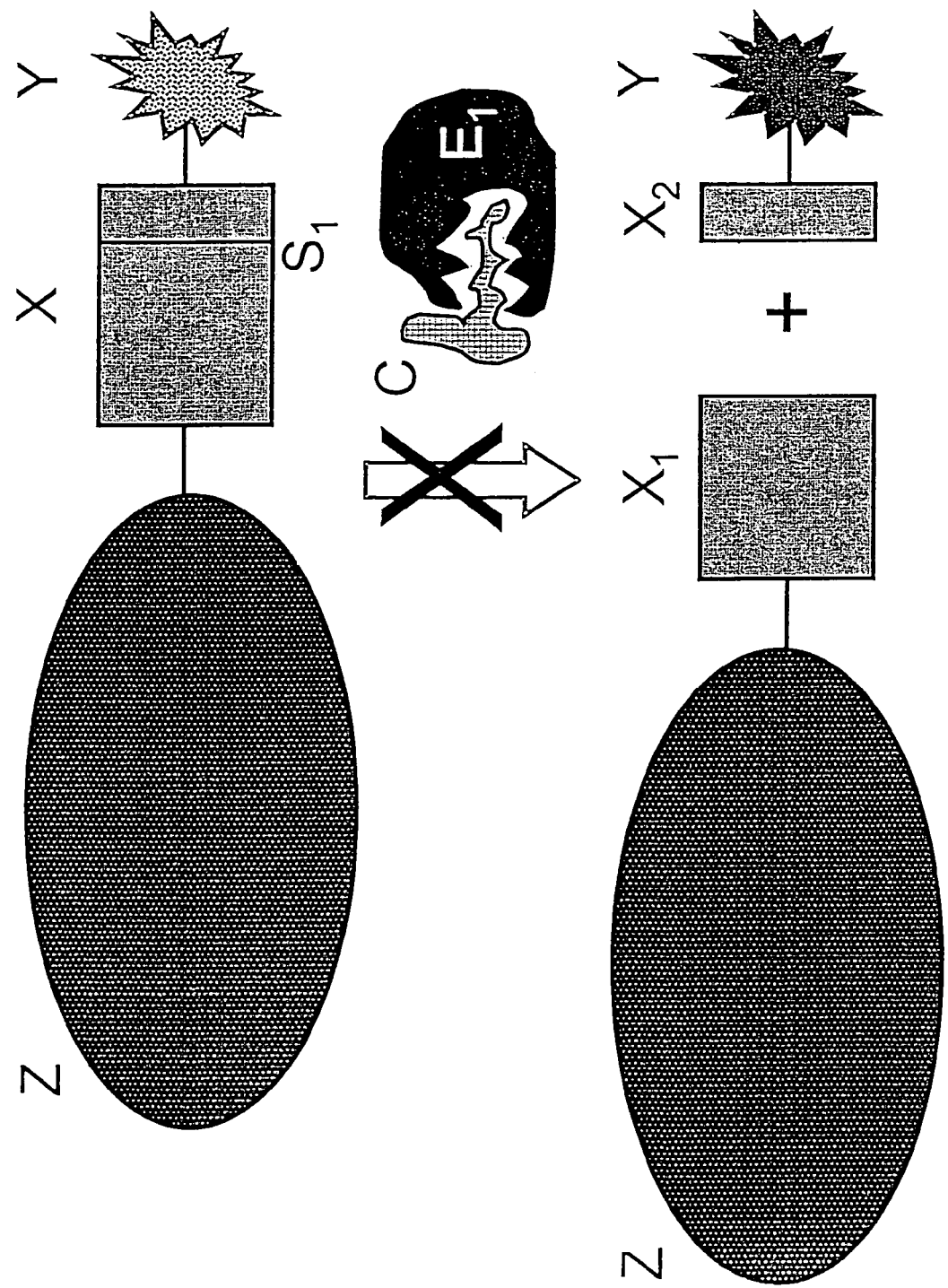

FIG. 11 schematically shows an embodiment of the substrate (Z-X-Y) according to the invention and its use for the identification of modulators (compounds "C") of enzyme-catalyzed cleaving reactions ("drug discovery"). In this Figure, the substrate has a single cleavage site $S_1$. Compounds which modulate (inhibit or activate) the enzymatic activity result in a lower amount (in the case of inhibition) or higher amount (in the case of activation) of products formed within a defined incubation time. Then, a molecular-weight-sensitive method can be used for relating the amount of products formed in the presence of a compound (this Figure) with the amount of products formed in the absence of a compound (see FIG. 10) in order to establish the degree of inhibition or activation of the enzymatic reaction. In this Figure, compound C inhibits the enzyme E1 completely, so that no products Z-$X_1$ and $X_2$-Y are formed. This corresponds to a degree of inhibition of 100%.

Figure 12:
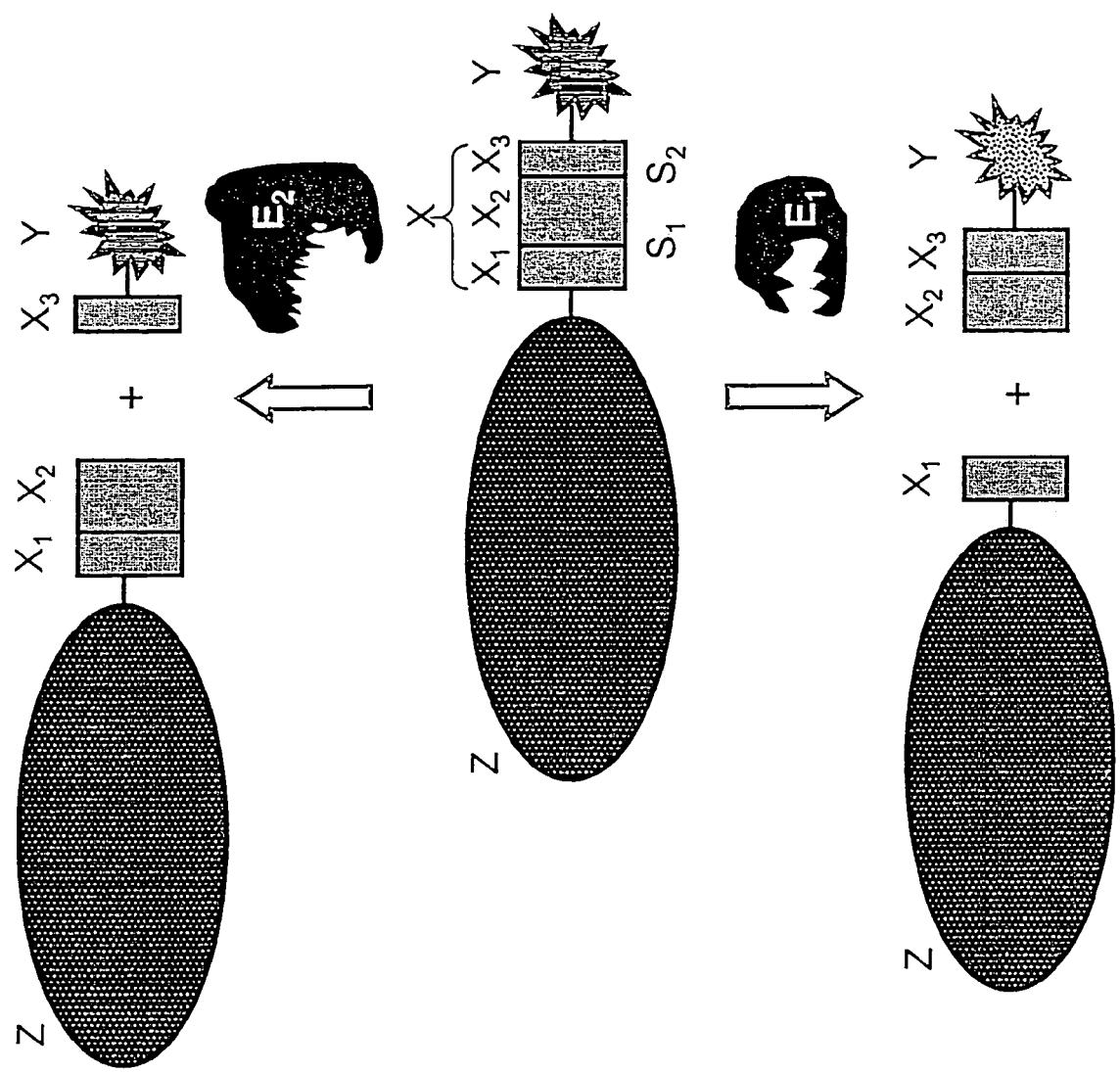

FIG. 12 shows another embodiment of the substrate (Z-X-Y) according to the invention and its use in the detection of sequentially performed enzyme-catalyzed cleavage reactions. In this Figure, the substrate has two cleavage sequences $S_1$ and $S_2$. The same substrate can be employed by incubation with one of the enzymes $E_1$ or $E_2$ which cleaves the substrate at the cleaving site $S_1$ or $S_2$ to form the products $Z-X_1$ and $X_2X_3-Y$ or $Z-X_1X_2$ and $X_3-Y$; the reaction can be detected by a molecular-weight-sensitive method. This embodiment of the substrate with several cleaving sites enables, firstly, to perform several drug discovery programs (search for modulators of enzyme $E_1$ or enzyme $E_2$) with only one substrate and, secondly, to determine the selectivity of modulators (Question: Is a modulator of enzyme $E_1$ also a modulator of enzyme $E_2$, or is a modulator of enzyme $E_2$ also a modulator of enzyme $E_1$?).

Figure 13:
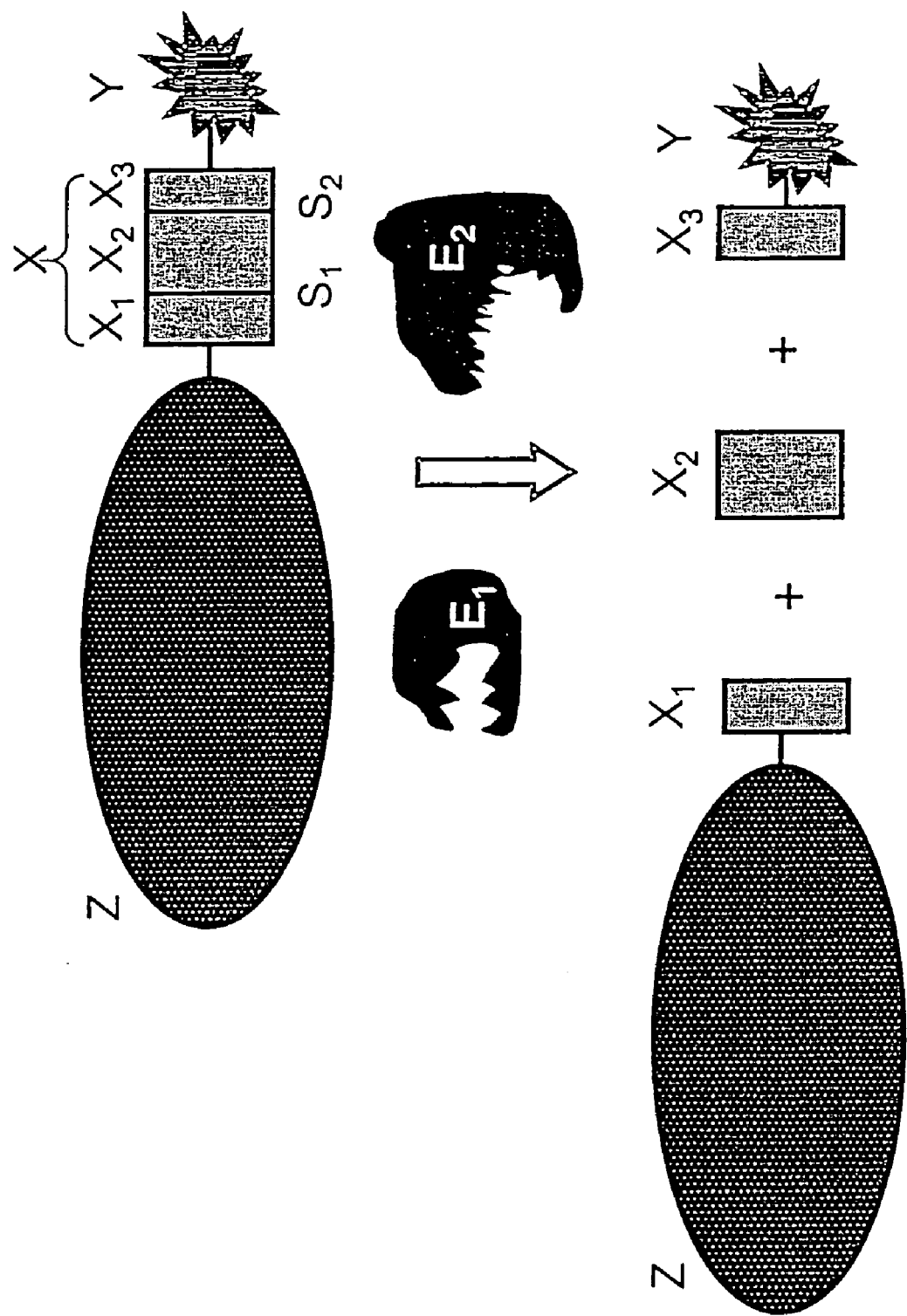

FIG. 13 shows an embodiment of the substrate (Z-X-Y) according to the invention and another use thereof in the detection of simultaneously performed enzyme-catalyzed cleavage reactions. In this Figure, the substrate has two cleavage sequences $S_1$ and $S_2$; however, the assay can also be performed with more than two cleavage sequences and a corresponding number of enzymes. The substrate can be cleaved into the cleavage products $Z-X_1$, $X_2$ and $X_3-Y$ by simultaneous incubation with the two enzymes $E_1$ and $E_2$. This assay can be employed for identifying modulators of a whole class of enzymes (e.g., modulators of caspases) in a drug discovery campaign, for example, for developing a broad-range medicament.

Figure 14:
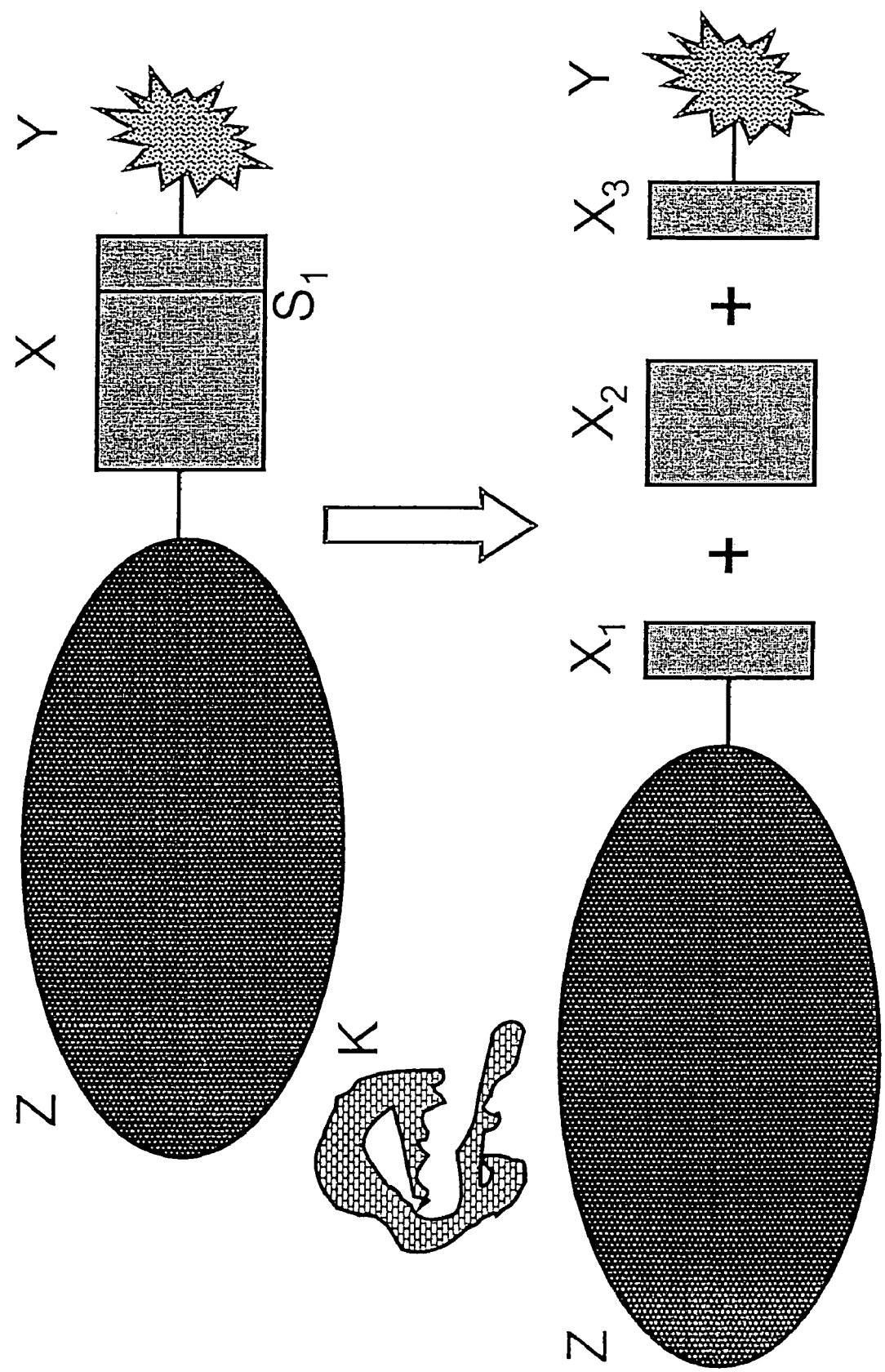

FIG. 14 shows an embodiment of the substrate (Z-X-Y) according to the invention and its use for the detection of contaminations K which result in the cleavage of the module X. In this Figure, the substrate has a single cleavage sequence $S_1$ which would be cleaved upon incubation with enzyme $E_1$. According to the invention, the module Z is inert towards the enzymatic reaction of E1. However, if the substrate is incubated with an arbitrary sample rather than with enzyme $E_1$, then it can be detected by a molecular-weight-sensitive method whether the substrate is nevertheless cleaved. Depending on circumstances, there may be formed more products (non-specific contamination) as compared to cleavage with the enzyme $E_1$. In this Figure, the contamination K results in the three products $Z-X_1$, $X_2$ and $X_3-Y$. If inhibitors which prevent the cleavage of Z are additionally added to the incubation, contaminations which cleave X can be selectively identified. The molecular-weight-sensitive method may also be used to detect specific contaminations.

Figure 15:
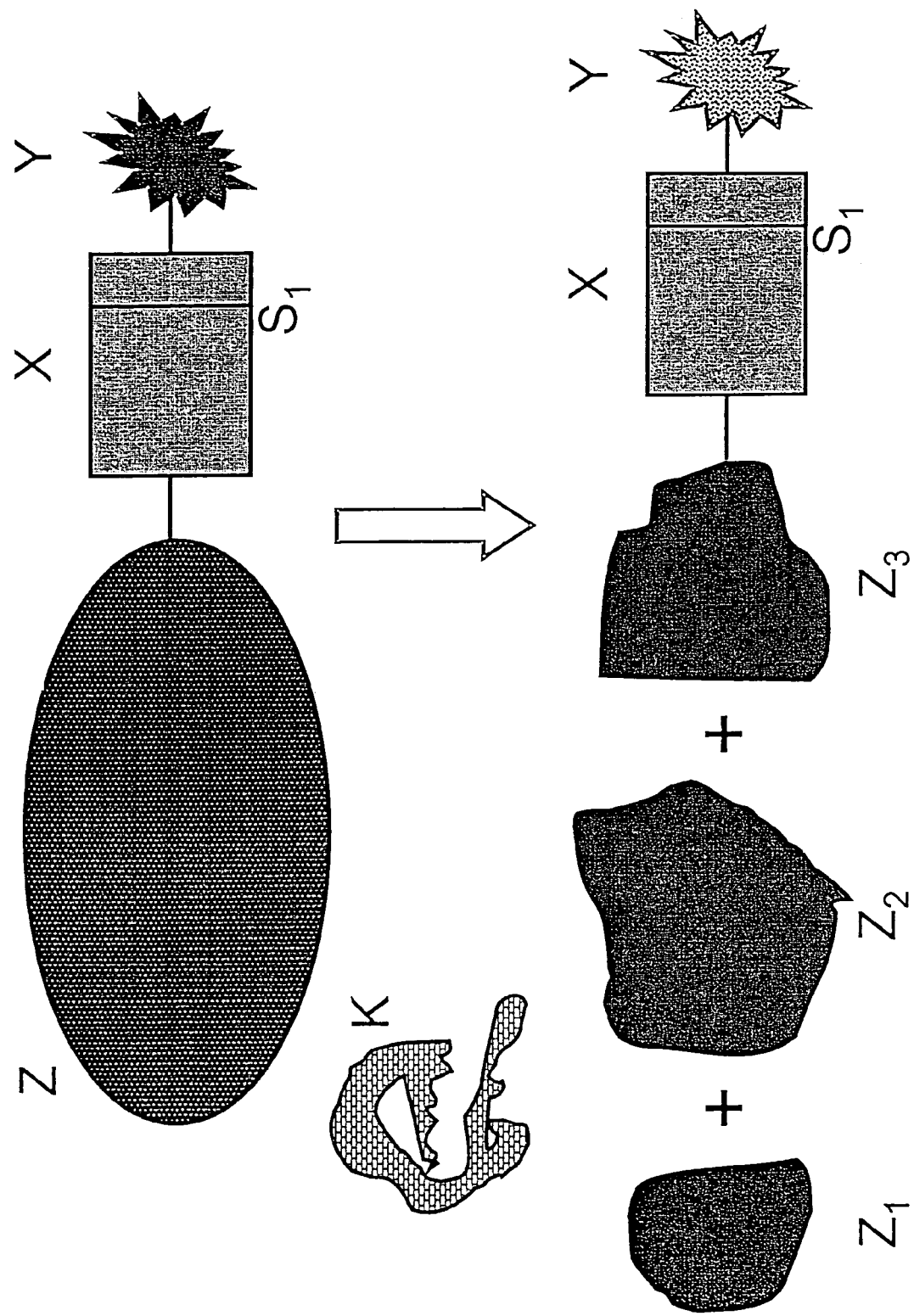

FIG. 15 shows an embodiment of the substrate (Z-X-Y) according to the invention and its use for the detection of contaminations K which result in the cleavage of the module Z. In this Figure, the substrate has a single cleavage sequence $S_1$ which would be cleaved upon incubation with enzyme $E_1$. According to the invention, the module Z is inert towards the enzymatic reaction of E1. However, if the substrate is incubated with an arbitrary sample rather than with enzyme $E_1$, then it can be detected by a molecular-weight-sensitive method whether the substrate is nevertheless cleaved. In this Figure, the contamination K results in the three products $Z_1$, $Z_2$ and $Z_3-X-Y$. If inhibitors which prevent the cleavage of X are additionally added to the incubation, contaminations which cleave Z can be selectively identified.

Figure 16:
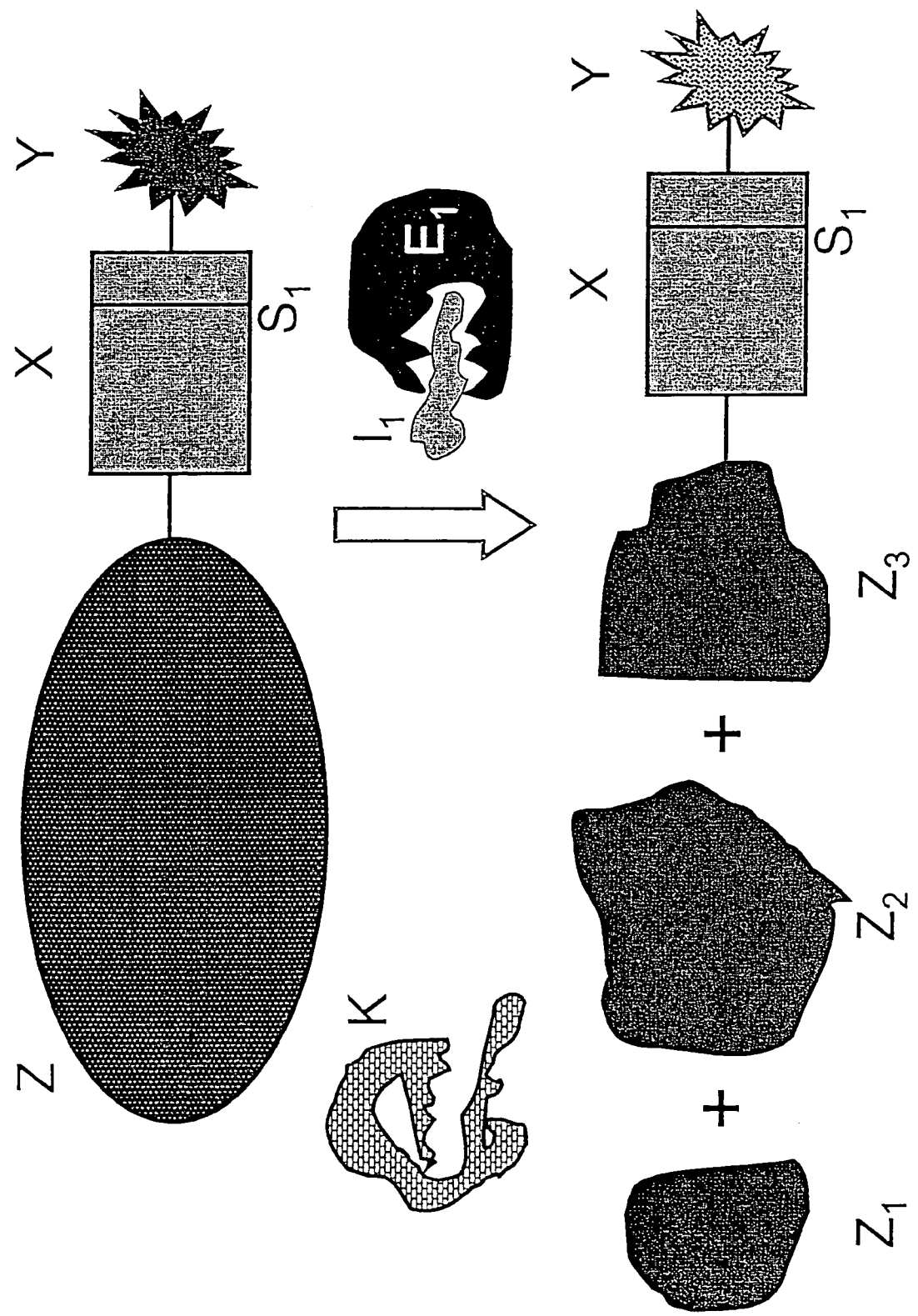

FIG. 16 shows an embodiment of the substrate (Z-X-Y) according to the invention and its use for the detection of contaminations K of the added charge of enzyme $E_1$ which cleaves the substrate at the cleavage site $S_1$. If the substrate is incubated with enzyme $E_1$ and additionally with an inhibitor $I_1$ of the enzymatic activity of the enzyme $E_1$, then it can be detected by a molecular-weight-sensitive method whether cleavage of the substrate nevertheless occurs. In this Figure, the three products $Z_1$, $Z_2$ and $Z_3-X-Y$ are formed.

Figure 17:
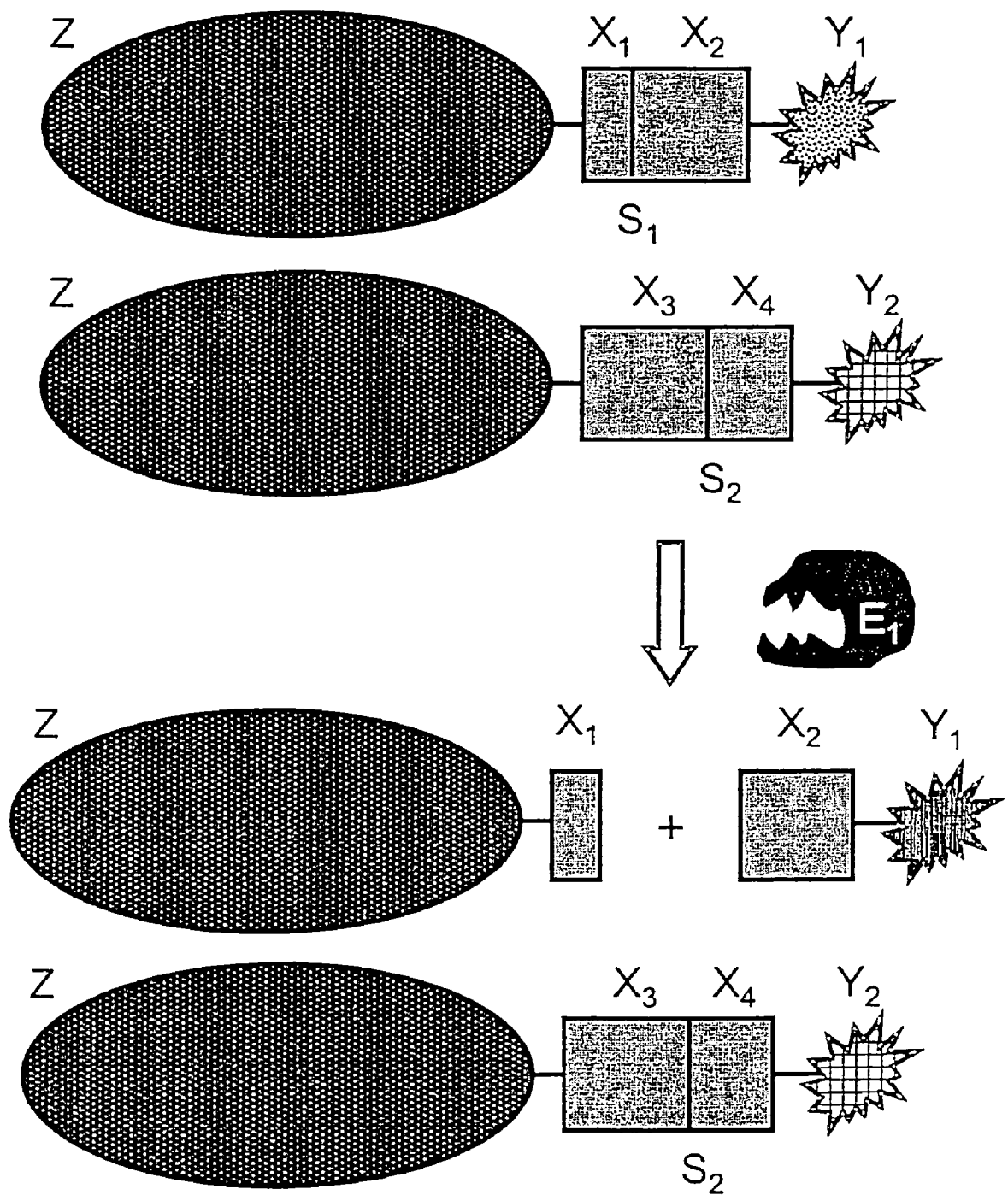

FIG. 17 schematically shows two embodiments of the substrate (Z-X-Y) according to the invention and its use for the determination of the substrate specificity of enzyme $E_1$. In the first embodiment of the substrate (Z-X-Y) according to the invention, the module X contains the cleavage site $S_1$. In the second embodiment of the substrate (Z-X-Y) according to the invention, the module X contains the cleavage site $S_2$. The two substrates contain different reporter modules $Y_1$ and $Y_2$. Especially, $Y_1$ and $Y_2$ can be different fluorescence dyes which emit fluorescence light at distinct wavelengths. If the two substrates are simultaneously incubated with the enzyme E1, then it can be detected by a molecular-weight-sensitive method which can distinguish between the two reporter modules (1) whether one of the two substrates has been cleaved, (2) which of the two substrates has been cleaved, and (3) whether both substrates have been cleaved. In this Figure, $E_1$ is specific for the substrate with the cleavage site $S_1$.

Figure 18:
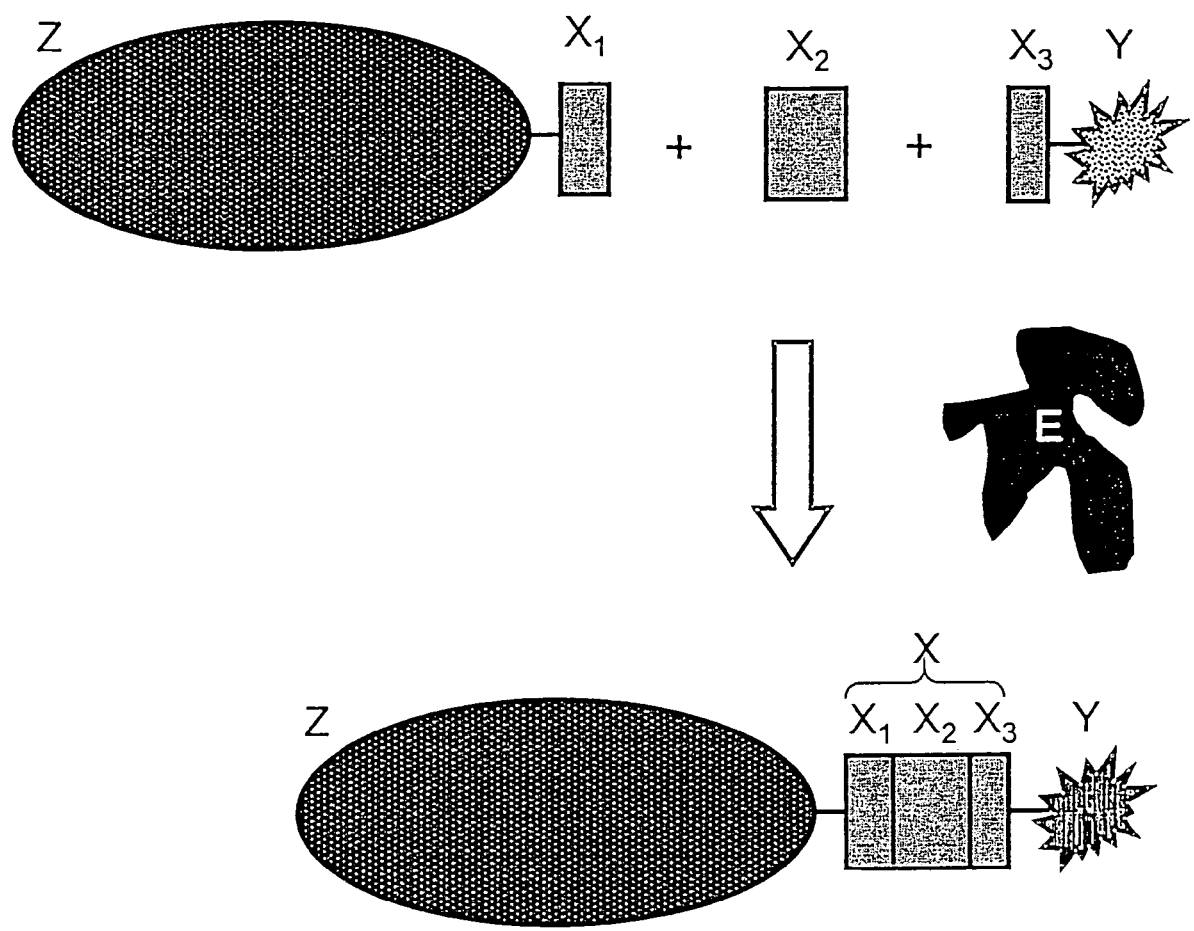

FIG. 18 shows the detection of the activity of an enzyme E which links individual substrates, by determining the linked product Z-X-Y containing the reporter module Y by means of a molecular-weight-sensitive method. This assay can also be used for the identification of modulators of enzyme activity. In this Figure, $Z-X_1$ and $X_3-Y$ are indirectly linked with each other through $X_2$.

FIG. 19 shows the practical use of the substrate described in FIG. 5 for the identification of caspase-3 inhibitors in a drug discovery campaign. The Figure gives a survey of the course and the results of the campaign. 193,146 potential modulators (compounds) were analyzed for their inhibitory effect on caspase-3. The compounds were employed in concentrations of 17 µM. In this campaign, 1.5% (primary hit rate) of the compounds showed an inhibition which exceeded a defined threshold value. These primary hits were tested again in the same concentration (17 µM) in multiple determinations for their inhibitory effect. In this way, the inhibitory effect of 229 compounds could be confirmed. The potency of these 229 compounds was established through the recording of dose-effect curves, which reflect the dependence of the inhibitory effect of a compound from the concentration employed of this compound. 27 compounds showed an $IC_{50}$ value which is lower than 50 µM. The mean value for the Z' factor, which is a measure of the robustness of an assay (Zhang, J.-H., et al. (1999). *J. Biomol. Screen.*, 4, 67-73), was 0.8 over the entire process. Z' values of larger than 0.5 indicate that the assay is excellent. Thus, the caspase-3 assay is very suitable for a drug discovery campaign.

Figure 20:
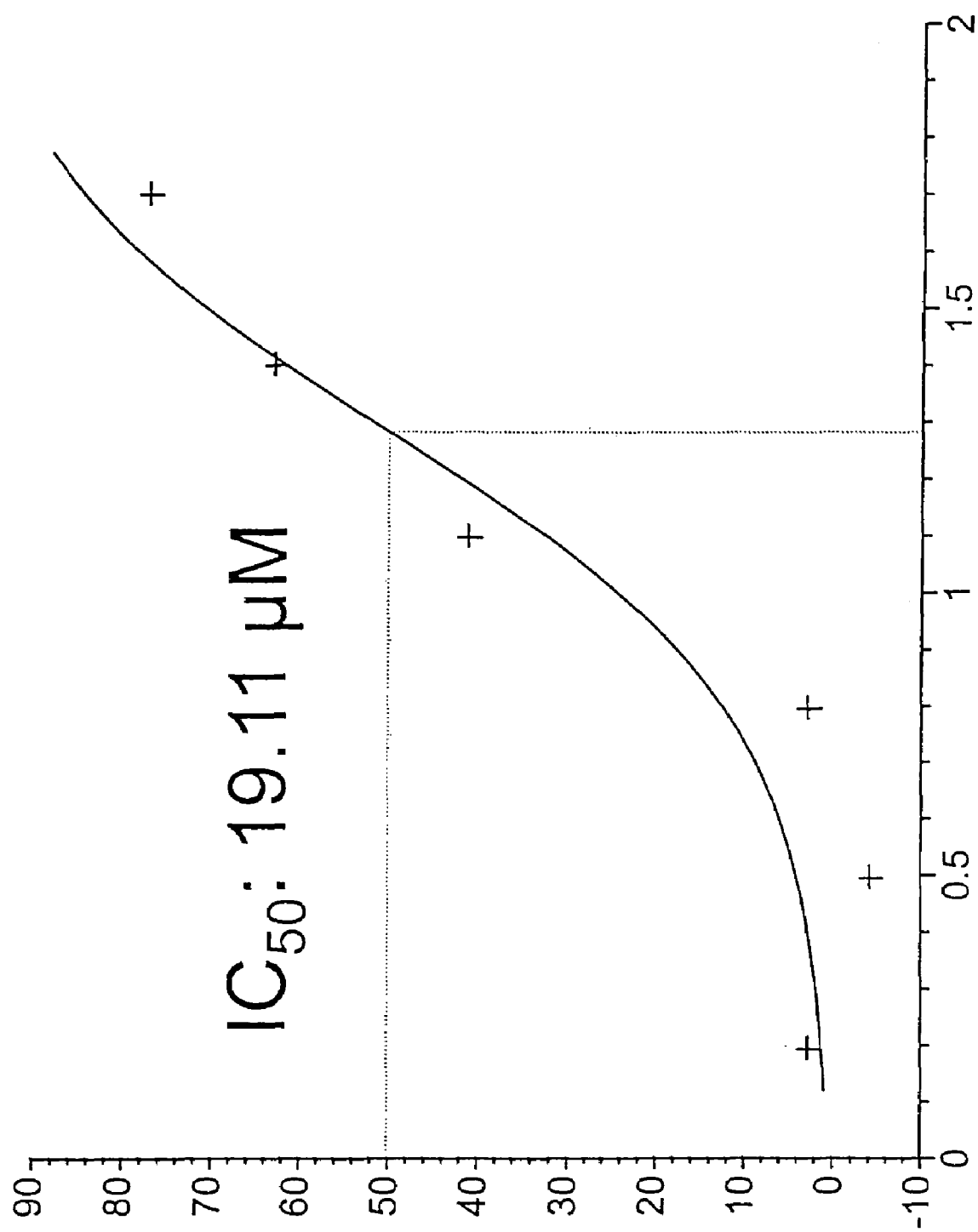

FIG. 20 illustratively shows the dose-effect curve for one of the 27 inhibitory compounds described in the legend to FIG. 19. The compound was examined for its inhibitors effect in 6 different concentrations (50 µM, 25 µM, 12.5 µM, 6.25 µM, 3.13 µM and 1.56 µM). An IC$_{50}$ value of 19.11 µM was determined.

EXAMPLE 1

Synthesis of a Caspase-3 Specific Substrate (Peptide No. 1):

The peptide with the sequence H-Gly-Asp-Glu-Val-Asp-Gly-Lys-OH was prepared by a standard solid-phase synthesis (Fmoc strategy). As the resin, Rink Amide MBHA resin with a loading of 0.54 mmol/g was used. A charge size of 20 µmol was selected (m$_{resin}$=37.0 mg). The activation of the amino acids was effected with 5 equivalents of HATU ([O-(7-azabenzotriazol-1-yl)-1,1,3,3-tetra-methyluronium hexafluorophosphate]) and 10 equivalents of DIPEA (N-ethyl-diisopropylamine) in DMF (N,N-dimethylformamide) (100 µmol HATU (38.0 mg) and 200 µmol DIPEA (34.0 µl)). The volume of the solvent was 5 ml per g of resin. Five equivalents of amino acid was employed. The reaction time was twice 1 hour (double coupling) at room temperature. The cleavage of the Fmoc protective group (fluorenyl-methoxycarbonyl) was performed with 20% piperidine in DMF. The cleavage time was twice 15 minutes. Each time after the couplings, and also after the Fmoc cleavage, the resin was washed with 3×DMF, 2×DMF/DCM (dichloromethane) [1:1], 3×DMF reagent grade. The Fmoc protective group on the N terminus was not removed. Thus, after the couplings of Fmoc-Lys(Mtt)-OH, Fmoc-Gly-OH, Fmoc-Asp(OtBu)-OH, Fmoc-Val-OH, Fmoc-Glu(OtBu)-OH, Fmoc-Asp(OtBu)-OH and Fmoc-Gly-OH, the following sequence results: Fmoc-Gly-Asp(OtBu)-Glu(OtBu)-Val-Asp(OtBu)-Gly-Lys(Mtt)-resin.

Coupling of the Dye to the Peptide:

For the labeling, 5 µmol of peptide-charged resin (9.3 mg) was employed. From the immobilized, completely protected Fmoc-GDEVDGK-OH, the Mtt (4-methyl-trityl) protective group on lysine was removed with 1 ml of 30% HFIP (1,1,1,3,3,3-hexafluoro-2-propanol) in DMF. Thereafter, washings were performed six times with 1 ml each of 30% HFIP in DMF. The subsequent washing was again effected with 3×DMF, 2×DMF/DCM, 3×DMF reagent grade. The primary amine formed was coupled with 1 equivalent (based on the charge size→5 µmol) of 5-TAMRA-NHS (5-carboxytetramethylrhodamine succinimidyl ester) in DMF. The reaction time was 8 hours at room temperature. After the labeling, the resin was washed. This results in the following intermediate product:

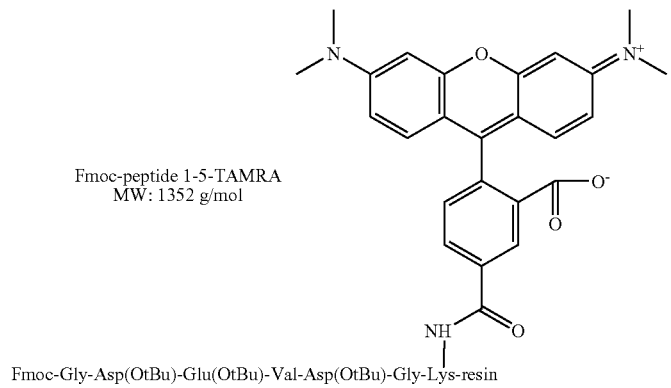

Fmoc-peptide 1-5-TAMRA
MW: 1352 g/mol

Coupling of a Linker to the Labeled Peptide:

After Fmoc cleavage with 20% piperidine in DMF, the labeled peptide 1 was modified with a linker (4-(N-maleimidomethyl)cyclohexane-1-carboxylic acid N-hydroxy-succinimide ester) to form the corresponding maleimide. For the coupling of the linker, 2 µmol of peptide resin (m=3.7 mg) was employed. Two equivalents of linker (based on the charge size) in DMF was charged onto the resin. The reaction time was 8 hours at room temperature. After washing the resin with 3×DMF, 3×DMF/DCM (1:1), 3×DCM and 3×tert-butyl methyl ether, the intermediate product was cleaved from the resin with TFA/TIPS/H$_2$O (95%/2.5%/2.5%). The cleaving time was 2.5 hours at room temperature. Thus, the following intermediate product is obtained:

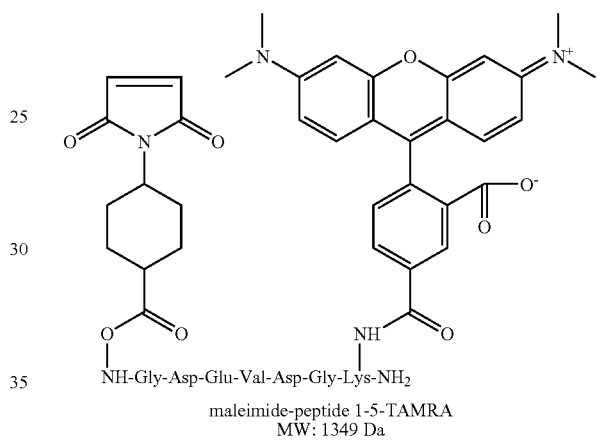

maleimide-peptide 1-5-TAMRA
MW: 1349 Da

The purification of the intermediate product was effected by HPLC. The mobile solvents employed were water+0.1% TFA (A) and methanol (B). A column (Waters, Symmetry 100, RP-18, 5 µm, 150 mm×19 mm) having a flow rate of 18 ml/min was used. The purification was effected with the following gradient: 0 min→10% B, 5 min→30% B, 45 min→70% B, 50 min→100% B. The characterization of the intermediate product was effected by LC-MS, MALDI-TOF-MS and UV/VIS spectroscopy.

Coupling of the maleimide-peptide1-5-TAMRA to DNA:

The intermediate product formed was converted to the desired final product using the lyophilized DNA double strand which was 5'-thiol-modified at one strand.

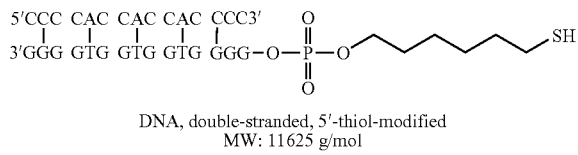

DNA, double-stranded, 5'-thiol-modified
MW: 11625 g/mol

Thus, the maleimide-peptide1-5-TAMRA (42 nmol) was taken up in 50 μl of 10 mM sodium phosphate buffer, pH 7.5. The number of equivalents of the peptide, based on the DNA, is 4. Thus, 10.4 nmol of DNA in 10 μl of H$_2$O was employed. The reaction time was 5 hours at 25° C.

acids was effected with 5 equivalents of HATU ([O-(7-azabenzotriazol-1-yl)-1,1,3,3-tetramethyl-uronium hexafluorophosphate]) and 10 equivalents of DIPEA (N-ethyldiisopropylamine) in DMF (N,N-dimethylformamide). This yields the following amounts per coupling: 100 μmol HATU (38.0 mg) and 200 μmol DIPEA (34.0 μl). The volume of the solvent was 5 ml per g of resin. Five equivalents of amino acid was employed. The reaction time was twice 1 hour (double coupling) at room temperature. The cleavage of the Fmoc protective group (fluorenylmethoxycarbonyl) was performed with 20% piperidine in DMF. The cleavage time was twice 15 minutes. Each time after the couplings, and also after the Fmoc cleavage, the resin was washed with 3×DMF, 2×DMF/DCM (dichloromethane) [1:1], 3×DMF reagent grade. The Fmoc protective group on the N terminus was not removed.

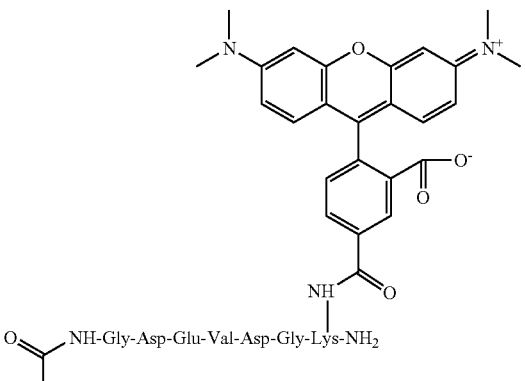

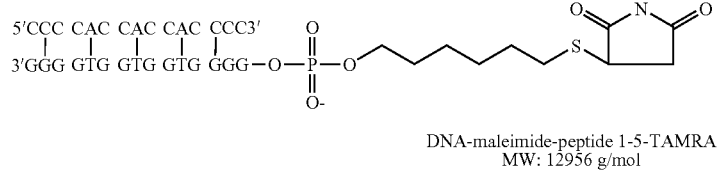

DNA-maleimide-peptide 1-5-TAMRA
MW: 12956 g/mol

The product was purified by HPLC over a gel column (Phenomenex, Biosep-SEC-S 2000, 300 mm×4.6 mm) with a flow rate of 0.15 ml/min at 12° C. An isocratic run with 10 mM sodium phosphate buffer, pH 7.5, was performed over 45 minutes. The characterization of the product was effected by UV/VIS spectroscopy, fluorescence spectroscopy, polarization and anisotropy determinations. The purity was established by an analytical run through the gel column.

Thus, the substrate specific for caspase 3 comprises: Asp-Glu-Val-Asp*-Gly, where Asp-Glu-Val-Asp is the recognition sequence of the protease and the cleavage is effected after Asp*.

EXAMPLE 2

Synthesis of a Caspase-8 Specific Substrate (Peptide No. 2):

The peptide with the sequence H-Gly-Ile-Glu-Thr-Asp-Gly-Lys-OH was prepared by a standard solid-phase synthesis (Fmoc strategy). As the resin, Rink Amide MBHA resin with a loading of 0.54 mmol/g was used. A charge size of 20 μmol was selected (37.0 mg). The activation of the amino acids was effected with 5 equivalents of HATU Thus, after the couplings of Fmoc-Lys(Mtt)-OH, Fmoc-Gly-OH, Fmoc-Asp(OtBu)-OH, Fmoc-Thr(tBu)-OH, Fmoc-Glu(OtBu)-OH, Fmoc-Ile-OH and Fmoc-Gly-OH, the following sequence results: Fmoc-Gly-Ile-Glu(OtBu)-Thr(tBu)-Asp(OtBu)-Gly-Lys(Mtt)-resin.

Coupling of the Dye to Peptide 2:

For the labeling, 5 μmol of peptide-charged resin (9.3 mg) was employed. From the immobilized, completely protected Fmoc-GIETDGK-OH, the Mtt (4-methyl-trityl) protective group on lysine was removed with 1 ml of 30% HFIP (1,1,1,3,3,3-hexafluoro-2-propanol) in DMF. Thereafter, washings were performed six times with 1 ml each of 30% HFIP in DMF. The subsequent washing was again effected with 3×DMF, 2×DMF/DCM, 3×DMF reagent grade. The primary amine formed was coupled with 1 equivalent (based on the charge size→5 μmol) of 5-TAMRA-NHS (5-carboxytetramethylrhodamine succinimidyl ester) in DMF. The reaction time was about 8 hours (over night) at room temperature. This now resulted in the following intermediate product:

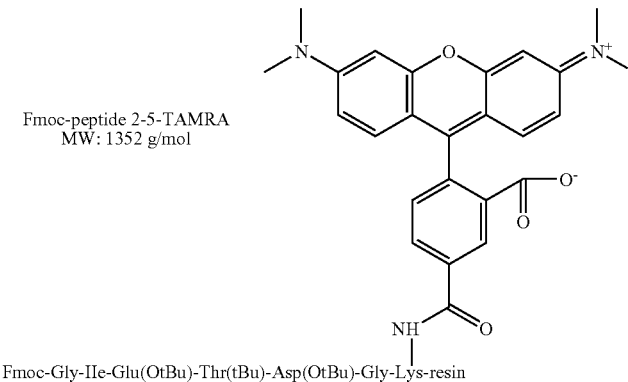

Fmoc-peptide 2-5-TAMRA
MW: 1352 g/mol

Fmoc-Gly-Ile-Glu(OtBu)-Thr(tBu)-Asp(OtBu)-Gly-Lys-resin

Coupling of a Linker to the Labeled Peptide 2:

After Fmoc cleavage with 20% piperidine in DMF, the peptide 2 was modified with a linker (4-(N-maleimidomethyl)cyclohexane-1-carboxylic acid N-hydroxy-succinimide ester) to form the corresponding maleimide. For the coupling of the linker, 2 μmol of peptide resin (m=3.7 mg) was employed. Two equivalents of linker (based on the charge size) in DMF was charged onto the resin. The reaction time was 8 hours at room temperature. After washing the resin with 3×DMF, 3×DMF/DCM (1:1), 3×DCM and 3×tert-butyl methyl ether, the intermediate product was cleaved from the resin with TFA/TIPS/H$_2$O (95%/2.5%/2.5%). The cleaving time was 2.5 hours at room temperature. Thus, the following intermediate product was obtained:

The purification of the intermediate product was effected by HPLC. The mobile solvents employed were water+0.1% TFA (A) and methanol (B). A column (Waters, Symmetry 100, RP-18, 5 μm, 150 mm×19 mm) having a flow rate of 18 ml/min was used. The purification was effected with the following gradient: 0 min→10% B, 5 min→30% B, 45 min→70% B, 50 min→100% B. The characterization of the intermediate product was effected by LC-MS, MALDI-TOF-MS and UV/VIS spectroscopy.

Coupling of the maleimide-peptide2-5-TAMRA to DNA:

The intermediate product formed was converted to the desired final product using the lyophilized 5'-thiol-modified DNA double strand.

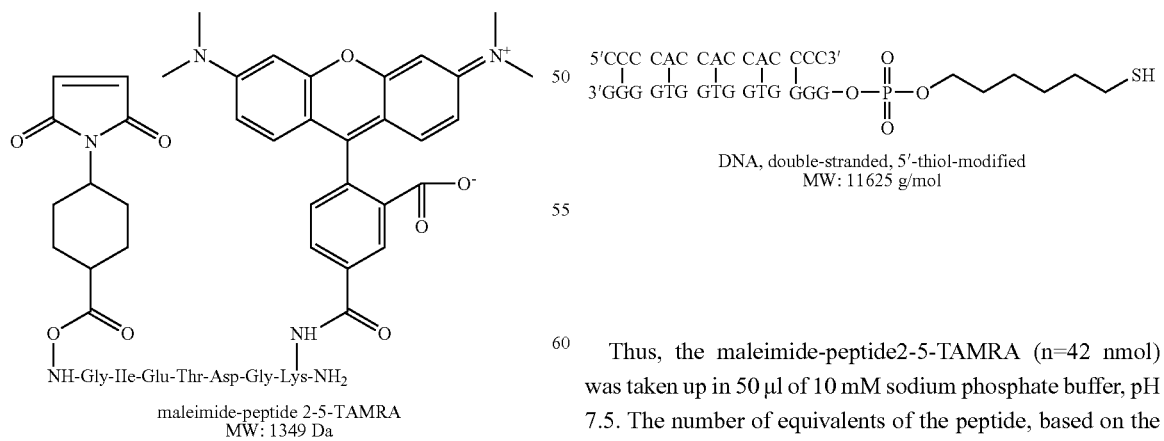

NH-Gly-Ile-Glu-Thr-Asp-Gly-Lys-NH$_2$ maleimide-peptide 2-5-TAMRA
MW: 1349 Da

DNA, double-stranded, 5'-thiol-modified
MW: 11625 g/mol

Thus, the maleimide-peptide2-5-TAMRA (n=42 nmol) was taken up in 50 μl of 10 mM sodium phosphate buffer, pH 7.5. The number of equivalents of the peptide, based on the DNA, is 4. Thus, 10.4 nmol of DNA in 10 μl of H$_2$O was employed. The reaction time was 5 hours at 25° C. This yielded the following final product:

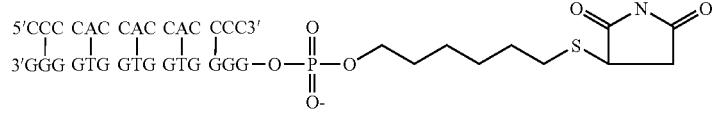

DNA-maleimide-peptide 2-5-TAMRA
MW: 12956 g/mol

The product was purified by HPLC over a gel column (Phenomenex, Biosep-SEC-S 2000, 300 mm×4.6 mm) with a flow rate of 0.15 ml/min at 12° C. An isocratic run with 10 mM sodium phosphate buffer, pH 7.5, was performed over 45 minutes. The characterization of the product was effected by UV/VIS spectroscopy, fluorescence spectroscopy, polarization and anisotropy determinations. The purity was established by an analytical run through the gel column.

Thus, the substrate specific for caspase 8 comprises: Ile-Glu-Thr-Asp*-Gly, where Ile-Glu-Thr-Asp is the recognition sequence of the protease and the cleavage is effected after Asp*.

EXAMPLE 3

Ultrahigh-throughput Screening (uHTS) for Inhibitors for Identifying Inhibitors of the Cysteine Protease Caspase-3 ("Drug Discovery"):

Apoptosis (programmed cell death, PCD) is a phenomenon which can be observed under physiological and pathological conditions. Apoptosis is the main form of cell death in eukaryotic organisms. It is found, inter alia, in the development of an embryo and in metamorphosis processes. In certain diseases (Alzheimer's, tumors, auto-immune diseases), the apoptotic process is disturbed. Key molecules in the apoptotic cascade are the so-called caspases. Therefore, inhibitors or activators of the caspases would be valuable for treating patients which suffer from a misregulation of apoptosis.

The cysteine protease caspase-3 is a central mediator of apoptosis in a wide variety of cells. A selective caspase-3 inhibitor could be employed for therapy, for example in strokes, in organ transplantations, in Parkinson's disease and in amyotrophic lateral sclerosis (ALS).

Therefore, the substrate described in Example 1 was also successfully employed for "ultrahigh-throughput screening" (uHTS) for inhibitors for identifying inhibitors of caspase-3 ("drug discovery"). The execution and results of this screening campaign are further described in the legend of FIG. 19.

EXAMPLE 4

Selectivity Determination of Caspase-3 Inhibitors Described in Example 3

The caspase-8 substrate described in Example 2 was employed for determining the selectivity of the caspase-3 inhibitors identified in the ultrahigh-throughput screening (uHTS). The method for the molecular-weight-sensitive detection of an enzyme-catalyzed cleavage reaction as already employed for caspase-3 could be successfully employed also in a caspase-8 assay.

The invention claimed is:

1. A method for detecting an enzyme-catalyzed cleavage reaction, comprising the following steps:

a) providing a modular chemical compound as a substrate for the enzyme comprising covalently linked modules X, Y, and Z having sequence motif:

i) Z-X-Y or ii) Y-X-Z, wherein

Z comprises a module which is inert with respect to the enzyme-catalyzed cleavage reaction;

X comprises a module having n cleavage sites which can be cleaved by the enzyme-catalyzed cleavage reaction into at least two cleavage products $X_1$ and $X_{n+1}$, respectively, n being an integer $\geq 1$; and Y comprises a fluorescent reporter module;

b) incubating the compound with the enzyme to form at least two cleavage products, the at least two cleavage products comprising:

i) $Z\text{-}X_1$ and $X_{n+1}\text{-}Y$, wherein the molecular weight of the cleavage product comprising $Z\text{-}X_1$ is at least fifty percent of the total molecular weight of the substrate, or ii) $Y\text{-}X_1$ and $X_{n+1}\text{-}Z$, wherein the molecular weight of the cleavage product comprising $X_{n+1}\text{-}Z$ is at least fifty percent of the total molecular weight of the chemical compound; and c) detecting the enzyme-catalyzed cleavage reaction by determining the cleavage product containing the reporter module Y, using molecular-weight-sensitive fluorescence spectroscopy.

* * * * *